(12) United States Patent
Watanabe et al.

(10) Patent No.: US 11,603,548 B2
(45) Date of Patent: Mar. 14, 2023

(54) FC-BINDING PROTEIN EXHIBITING IMPROVED ALKALINE RESISTANCE, METHOD FOR PRODUCING SAID PROTEIN, ANTIBODY ADSORBENT USING SAID PROTEIN, AND METHOD FOR SEPARATING ANTIBODY USING SAID ANTIBODY ADSORBENT

(71) Applicant: TOSOH CORPORATION, Yamaguchi (JP)

(72) Inventors: Ryoko Watanabe, Kanagawa (JP); Satoshi Endo, Kanagawa (JP); Yosuke Terao, Kanagawa (JP); Seigo Oe, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 228 days.

(21) Appl. No.: 16/759,039

(22) PCT Filed: Oct. 26, 2018

(86) PCT No.: PCT/JP2018/040004
§ 371 (c)(1),
(2) Date: Apr. 24, 2020

(87) PCT Pub. No.: WO2019/083048
PCT Pub. Date: May 2, 2019

(65) Prior Publication Data
US 2021/0261605 A1    Aug. 26, 2021

(30) Foreign Application Priority Data

| Oct. 27, 2017 | (JP) | ................ JP2017-207810 |
| Jan. 11, 2018 | (JP) | ................ JP2018-002868 |
| Jun. 11, 2018 | (JP) | ................ JP2018-111357 |

(51) Int. Cl.
| C07K 1/22 | (2006.01) |
| C07K 14/735 | (2006.01) |
| C12P 21/02 | (2006.01) |
| C07K 1/16 | (2006.01) |
| C07K 16/28 | (2006.01) |

(52) U.S. Cl.
CPC ................ *C12P 21/02* (2013.01); *C07K 1/16* (2013.01); *C07K 1/22* (2013.01); *C07K 14/70535* (2013.01); *C07K 16/283* (2013.01)

(58) Field of Classification Search
CPC ................ C07K 1/22; C07K 16/70535; C07K 14/70535
See application file for complete search history.

(56) References Cited

U.S. PATENT DOCUMENTS

| 2013/0079499 A1 | 3/2013 | Hatayama et al. |
| 2013/0084648 A1 | 4/2013 | Bolton et al. |
| 2016/0222081 A1 | 8/2016 | Asaoka et al. |
| 2017/0218044 A1 | 8/2017 | Asaoka et al. |

FOREIGN PATENT DOCUMENTS

| EP | 3584257 A1 | 12/2019 |
| JP | 1999(H11)-511649 A | 10/1999 |
| JP | 2002-531086 A | 9/2002 |
| JP | 2013-059313 | 4/2013 |
| JP | 2013/120929 A1 | 8/2013 |
| JP | 2014-027916 | 2/2014 |
| JP | 2014-527518 A | 10/2014 |
| JP | 2015-019615 A | 2/2015 |
| JP | 2015-83558 A | 4/2015 |
| JP | 2015-086216 | 5/2015 |
| JP | 2016-169197 | 9/2016 |
| JP | 2017-118871 | 7/2017 |
| WO | 1996/34953 A2 | 11/1996 |
| WO | 2000/32767 A1 | 6/2000 |
| WO | 2003/054213 A2 | 7/2003 |
| WO | 2004/062619 A2 | 7/2004 |
| WO | 2011/111393 | 9/2011 |
| WO | 2013/013193 A1 | 1/2013 |
| WO | 2015/041303 | 3/2015 |
| WO | 2015/199154 | 12/2015 |
| WO | 2018/150973 A1 | 8/2018 |

OTHER PUBLICATIONS

Bruhns et al., "Blood, 16", 2009, pp. 3716-3725.
Chen et al., "ACM Chem. Biol., 12", 2017, pp. 1335-1345.
Galon et al., "Eur. J. Immunol. 27", 1997, pp. 1932-1997.
Koene et al., "Blood, 90", 1997, pp. 1109-1114.
Takai, "Jpn. J. Clin. Immunol. 28", 2005, pp. 318-326.
Official Communication issued in International Bureau of WIPO Patent Application No. PCT/JP2018/040004, dated Jan. 29, 2019.
Kiyoshi, M. et al., Nature Communications, vol. 6, No. 1, Apr. 30, 2015 (Apr. 30, 2015).
K. A. Rogers et al.: "IgG Fc Receptor III Homologues in Nonhuman Primate Species: Genetic Characterization and Ligand Interactions", The Journal of Immunology, vol. 177, No. 6, Sep. 15, 2006, pp. 3848-3856.
Guozhang Zou et al.: "Chemoenzymatic Synthesis and Fc[gamma] Receptor Binding of Homogeneous Glycoforms of Antibody Fc Domain. Presence of a Bisecting Sugar Moiety Enhances the Affinity of Fc to Fc[gamma]IIIa Receptor", Journal of the American Chemical Society, vol. 133, No. 46, Nov. 23, 2011, pp. 18975-18991.
M. Shibata-Koyama et al: "The N-linked oligosaccharide at Fc RIIIa Asn-45: an inhibitory element for high Fc RIIIa binding affinity to IgG glycoforms lacking core fucosylation", Glycobiology, vol. 19, No. 2, Oct. 24, 2008, pp. 126-134.

(Continued)

*Primary Examiner* — Jeffrey E. Russel
(74) *Attorney, Agent, or Firm* — Greenblum & Bernstein, P.L.C.

(57) ABSTRACT

An Fc-binding protein exhibiting improved alkaline resistance, a method for producing the protein, an antibody adsorbent obtained by immobilizing the protein on a carrier, and a method for separating an antibody using the adsorbent.

9 Claims, 4 Drawing Sheets

Specification includes a Sequence Listing.

(56) References Cited

OTHER PUBLICATIONS

J. L. Ellsworth et al: "Generation of a high-affinity Fc receptor by Ig-domain swapping between human CD64A and D16A", Protein Engineering, Design and Selection, vol. 23, No. 4, Feb. 11, 2010, pp. 299-309.
Ferrara Claudia et al: "The carbohydrate at Fc Gamma RIIIa Asn-162-an element required for high affinity binding to non-fucosylated IgG glycoforms", Journal of Biological Chemistry, American Society for Biochemistry and Molecular Biology, US, vol. 281, No. 8, Feb. 24, 2006, pp. 5032-5036.
Database UniProt[Online] Oct. 19, 2011, "SubName: Full= Uncharacterized protein{ECO:0000313| Ensembl: ENSNLEP00000017512{;", XP002770838, retrieved from EBI accession No. UNIPROT: G1RW85 Database accession No. G1RW85.
Database UniProt[Online] Jul. 27, 2011, "SubName: Full= Uncharacterized protein{ECO:0000313| Ensembl: ENSCJA00000008582};", XP002770839, retrieved from EBI accession No. UNIPROT: F7IPS7 Database accession No. F7IPS7.
Hibbs M L et al.: "Membrane-Proximal Ig-Like Domain of FCGAM-MARIII(CD16) Containes Residues Critical for Ligand Binding", The Journal of Immunology, The American Association of Immunologists, US, vol. 152, May 1, 1994, pp. 4466-4474.
Shinkawa.T., J.Biol.Chem., 278, 3466-3473 (2003).
Database Geneseq [Online] (Mar. 18, 2010) "Human IgG Fc gamma receptor IIIb extracellular domain protein, SEQ ID: 13" XP002776987 retrieved from EBI accession No. GSP: AXU36851Database accession No. AXU36851 * sequence *.
Journal of Chromatography A, 720, 217-225, 1996.
MAbs, 5(4), 576-586, 2013.
P. Sonderman et al., Nature, 406, 267-2735, 2000.

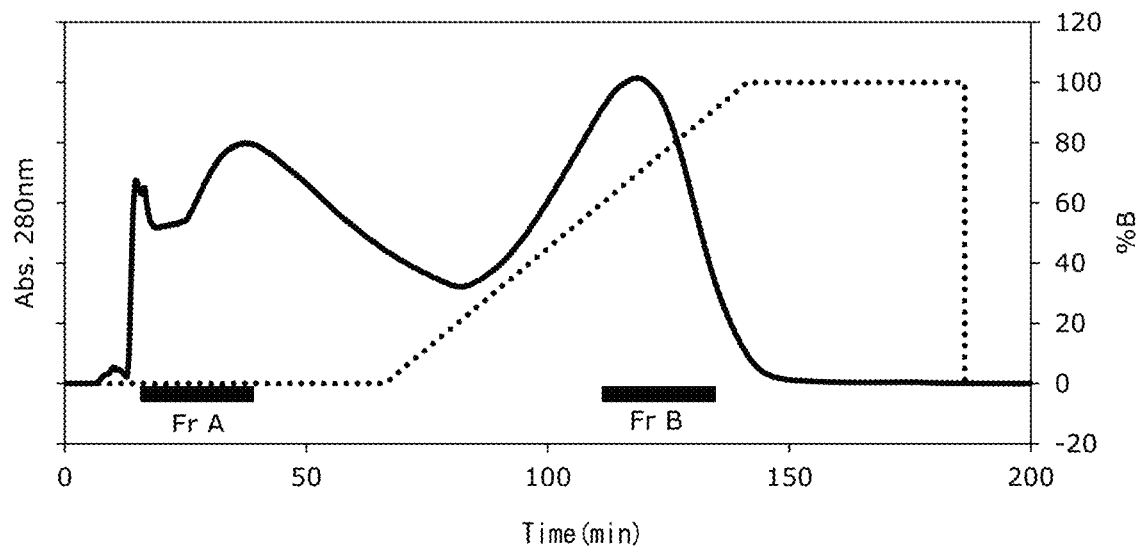

FC-BINDING PROTEIN EXHIBITING IMPROVED ALKALINE RESISTANCE, METHOD FOR PRODUCING SAID PROTEIN, ANTIBODY ADSORBENT USING SAID PROTEIN, AND METHOD FOR SEPARATING ANTIBODY USING SAID ANTIBODY ADSORBENT

SEQUENCE LISTING

The instant application contains a Sequence Listing which has been submitted electronically in ASCII format and is hereby incorporated by reference in its entirety. Said ASCII copy, created on Apr. 27, 2021, is named P60255_SL.txt and is 36,855 bytes in size.

FIELD

The present invention relates to an Fc-binding protein having an affinity for an immunoglobulin. More specifically, the invention relates to an Fc-binding protein with alkali stability (alkali resistance) that is improved over the wild-type, to a method for producing the protein, to an antibody adsorbent obtained by immobilizing the protein on an insoluble support, and to a method of isolating an antibody using the antibody adsorbent.

The invention further relates to an Fc-binding protein with improved productivity by transformants, by having amino acid residues at specific positions in human FcγRIIIa substituted with other specific amino acid residues.

BACKGROUND

Fc receptors are a group of molecules that bind to the Fc regions of immunoglobulin molecules. The individual molecules recognize single immunoglobulin isotypes, or those of the same group, by recognition domains on the Fc receptor, depending on the recognition domain belonging to an immunoglobulin superfamily. This determines which accessory cells will be driven in an immune response. Fc receptors can be further classified into several subtypes, namely Fcγ receptors which are receptors for IgG (immunoglobulin G), Fcε receptors that bind to the Fc region of IgE, and Fcα receptors that bind to the Fc region of IgA. Each of these receptors have still more detailed classifications, with reported Fcγ receptors comprising FcγRI, FcγRIIa, FcγRIIb, FcγRIIIa and FcγRIIIb (NPL 1).

Among the Fcγ receptors, FcγRIIIa receptors are found on the cell surfaces of natural killer cells (NK cells) and macrophages, and they are important receptors involved in the activation of the important human immunomechanism ADCC (antibody-dependent cell-mediated cytotoxicity). The affinity between FcγRIIIa and human IgG is reported to be a binding constant (ka) of $\leq 10^7$ $M^{-1}$, which represents the strength of binding (NPL 2). Affinity between FcγRIIIa and antibodies is known to differ according to differences in the sugar chain structures of the antibodies (NPL 3). The amino acid sequence of wild-type human FcγRIIIa (SEQ ID NO: 1) has been published in public databases such as UniProt (Accession number: P08637). Moreover, the functional domain on the structure of human FcγRIIIa, the signal peptide sequence for spanning of the cell membrane, and the position of the cell membrane-spanning region have likewise been published. FIG. 1 shows a structural diagram of human FcγRIIIa. The numbers in FIG. 1 represent amino acid numbers, the numbers corresponding to the amino acid numbers in SEQ ID NO: 1. Specifically, the region from methionine (Met) at position 1 to alanine (Ala) at position 16 of SEQ ID NO: 1 is the signal sequence (S), the region from glycine (Gly) at position 17 to glutamine (Gln) at position 208 is the extracellular domain (EC), the region from valine (Val) at position 209 to valine (Val) at position 229 is the cell membrane-spanning region (TM), and the region from lysine (Lys) at position 230 to lysine (Lys) at position 254 is the intracellular region (C). It is known that FcγRIIIa binds particularly strongly to IgG1 and IgG3, among the human IgG subclasses from IgG1 to IgG4, while binding weakly to IgG2 and IgG4.

Because the sugar chain structure of an antibody greatly contributes to the drug efficacy and stability of an antibody drug, it is extremely important to control the sugar chain structure during production of the antibody drug. Since FcγRIIIa recognizes the sugar chain structure of an antibody, an adsorbent obtained by immobilizing FcγRIIIa on an insoluble support can separate the antibody by the difference in affinity based on sugar chain structure (PTLs 2 and 3). The adsorbent is therefore useful for process analysis and fractionation during production of an antibody drug. However, when it is attempted to carry out industrial production of an antibody drug using such an adsorbent, since there is no alkali resistance with wild-type FcγRIIIa and reuse of the adsorbent by alkali cleaning is difficult, it has been unsuitable for industrial production.

PTL 1 discloses an Fc-binding protein with increased alkali resistance by replacing amino acid residues at specific positions with other amino acid residues among the amino acid residues of the extracellular domain of the wild-type FcγRIIIa. However, the alkali resistance is still not adequate even with the Fc-binding protein disclosed in PTL 1, and production cost has been an issue when it is used for industrial production of an antibody drug.

Human FcγRIIIa has a gene polymorphism with a type wherein the amino acid at position 176 of SEQ ID NO: 1 is phenylalanine (the SEQ ID NO: 1 type) and a type wherein it is valine (the SEQ ID NO: 19 type, published in GenBank (AAH17865.1)), the valine type being known to have high antibody affinity and the phenylalanine type being known to have low antibody affinity (NPLs 4 and 5).

CITATION LIST

Patent Literature

[PTL 1] Japanese Unexamined Patent Publication No. 2017-118871
[PTL 2] Japanese Unexamined Patent Publication No. 2015-086216
[PTL 3] Japanese Unexamined Patent Publication No. 2016-169197

Non-Patent Literature

[NPL 1] Takai. T., Jpn. J. Clin. Immunol. 28, 318-326, 2005
[NPL 2] J. Galon et al., Eur. J. Immunol. 27, 1928-1932, 1997
[NPL 3] C. L. Chen et al., ACS Chem. Biol., 12, 1335-1345, 2017
[NPL 4] H. R. Koene et al., Blood, 90, 1109-1114, 1997
[NPL 5] P. Bruhns et al., Blood, 16, 3716-3725, 2009

SUMMARY

Technical Problem

It is one object of the invention to provide an Fc-binding protein with increased alkali stability (alkali resistance), a method for producing the protein and an antibody adsorbent using the protein.

Since FcγRIIIa recognizes antibody sugar chain structures as mentioned above, an adsorbent obtained by immobilizing FcγRIIIa on an insoluble support is useful for process analysis and fractionation during production of antibody drugs. However, when industrial production of an antibody drug is attempted using the adsorbent, productivity in transformants with conventional FcγRIIIa has been poor, which has posed a problem in terms of cost. It is therefore at least one object of the invention to provide amino acid-substituted FcγRIIIa with increased productivity in transformants, compared to conventional FcγRIIIa.

Solution to Problem

As a result of diligent research conducted with the aim of achieving this object, the present inventors have identified an amino acid residue involved in increased stability of human FcγRIIIa, and have found that mutants in which said amino acid residue has been substituted with other amino acid residues have excellent stability against alkalis, and we have thus completed this invention. The present inventors have also comprehensively replaced the amino acid residue at position 176 with other amino acid residues in the amino acid sequence of human FcγRIIIa listed as SEQ ID NO: 1, and as a result we have found an amino acid-substituted form with increased productivity by transformants compared to conventional FcγRIIIa. The present inventors have completed this invention based on this knowledge. Specifically, the invention encompasses the following aspects [1] to [11].

[1]
An Fc-binding protein comprising amino acid residues with amino acid substitutions at least at the following 35 locations among the amino acid residues from glycine at position 33 to glutamine at position 208 in the amino acid sequence listed as SEQ ID NO: 4:
  (1) A substitution of glycine for glutamic acid at position 37 of SEQ ID NO: 4;
  (2) A substitution of methionine for leucine at position 39 of SEQ ID NO: 4;
  (3) A substitution of glutamic acid for valine at position 43 of SEQ ID NO: 4;
  (4) A substitution of isoleucine for phenylalanine at position 45 of SEQ ID NO: 4;
  (5) A substitution of proline for glutamine at position 49 of SEQ ID NO: 4;
  (6) A substitution of asparagine for tyrosine at position 51 of SEQ ID NO: 4;
  (7) A substitution of glutamine for lysine at position 56 of SEQ ID NO: 4;
  (8) A substitution of arginine for glutamine at position 64 of SEQ ID NO: 4;
  (9) A substitution of histidine for tyrosine at position 67 of SEQ ID NO: 4;
  (10) A substitution of aspartic acid for glutamic acid at position 70 of SEQ ID NO: 4;
  (11) A substitution of aspartic acid for asparagine at position 72 of SEQ ID NO: 4;
  (12) A substitution of arginine for serine at position 81 of SEQ ID NO: 4;
  (13) A substitution of proline for serine at position 84 of SEQ ID NO: 4;
  (14) A substitution of phenylalanine for tyrosine at position 90 of SEQ ID NO: 4;
  (15) A substitution of isoleucine for phenylalanine at position 91 of SEQ ID NO: 4;
  (16) A substitution of serine for alanine at position 94 of SEQ ID NO: 4;
  (17) A substitution of serine for threonine at position 96 of SEQ ID NO: 4;
  (18) A substitution of serine for asparagine at position 108 of SEQ ID NO: 4;
  (19) A substitution of glutamic acid for valine at position 133 of SEQ ID NO: 4;
  (20) A substitution of valine for lysine at position 135 of SEQ ID NO: 4;
  (21) A substitution of glycine for glutamic acid at position 137 of SEQ ID NO: 4;
  (22) A substitution of glutamic acid for aspartic acid at position 138 of SEQ ID NO: 4;
  (23) A substitution of arginine for lysine at position 148 of SEQ ID NO: 4;
  (24) A substitution of methionine for threonine at position 156 of SEQ ID NO: 4;
  (25) A substitution of phenylalanine for tyrosine at position 157 of SEQ ID NO: 4;
  (26) A substitution of valine for glycine at position 163 of SEQ ID NO: 4;
  (27) A substitution of valine for tyrosine at position 174 of SEQ ID NO: 4;
  (28) A substitution of glutamic acid for lysine at position 181 of SEQ ID NO: 4;
  (29) A substitution of serine for phenylalanine at position 187 of SEQ ID NO: 4;
  (30) A substitution of arginine for serine at position 194 of SEQ ID NO: 4;
  (31) A substitution of lysine for asparagine at position 196 of SEQ ID NO: 4;
  (32) A substitution of glycine for glutamic acid at position 200 of SEQ ID NO: 4;
  (33) A substitution of alanine for threonine at position 201 of SEQ ID NO: 4;
  (34) A substitution of aspartic acid for asparagine at position 203 of SEQ ID NO: 4;
  (35) A substitution of valine for isoleucine at position 206 of SEQ ID NO: 4; and having antibody-binding activity
[2]
The Fc-binding protein according to [1], which is one of the following (a), (b) or (c):
(a) An Fc-binding protein comprising, among the amino acid residues from glycine at position 33 to glutamine at position 208 in the amino acid sequence listed as SEQ ID NO: 4:
  (i) the amino acid substitutions (1) to (35) listed above, and
  (ii) an amino acid residue with one or more substitutions, deletions, insertions or additions of one or more amino acids other than those of (i);
(b) An Fc-binding protein comprising the amino acid substitutions of (1) to (35), and having an amino acid sequence having at least 70% homology with an amino acid sequence comprising the amino acid residues from glycine at position 33 to glutamine at position 208 of the amino acid sequence listed as SEQ ID NO: 4;
(c) An Fc-binding protein comprising an amino acid sequence with the amino acid substitutions of (1) to (35) in an amino acid sequence having at least 70% homology with the amino acid sequence from glycine at position 33 to glutamine at position 208 of the amino acid sequence listed as SEQ ID NO: 4, and having antibody binding activity.

[3]
The Fc-binding protein according to [1] or [2], having at least one of the following amino acid substitutions:

(36) A substitution of isoleucine for valine at position 192 of SEQ ID NO: 4;

(37) A substitution of alanine for valine at position 192 of SEQ ID NO: 4;

(38) A substitution of tyrosine for valine at position 192 of SEQ ID NO: 4.

[4]
The Fc-binding protein according to any one of [1] to [3], comprising at least the amino acid residues from glycine at position 33 to glutamine at position 208 of the amino acid sequence listed as SEQ ID NO: 7, 9 or 11.

[5]
A polynucleotide encoding the Fc-binding protein according to any one of [1] to [4].

[6]
An expression vector comprising the polynucleotide according to [5].

[7]
A transformant capable of producing Fc-binding protein, obtained by transforming a host with the expression vector according to [6].

[8]
The transformant according to [7], wherein the host is *E. coli*.

[9]
A method for producing Fc-binding protein, comprising a step of producing Fc-binding protein by culturing the transformant according to [7] or [8], and a step of recovering the produced Fc-binding protein from the cultured product.

[10]
An antibody adsorbent obtained by immobilizing the Fc-binding protein according to any one of [1] to [4] on an insoluble support.

[11]
An antibody separating method comprising a step of adding an antibody-containing solution to a column packed with an adsorbent according to [10] and adsorbing the antibody onto the adsorbent, and a step of using an eluent to elute the antibody adsorbed on the adsorbent.

[12]
The separating method according to [11], wherein antibodies with different sugar chain structures are separated based on differences in their affinity for Fc-binding protein.

The present invention will now be explained in greater detail.

The Fc-binding protein of the invention is a protein having affinity for the Fc region of an antibody, wherein the protein comprising at least the amino acid residues from glycine at position 33 to glutamine at position 208 (glycine at position 17 and glutamine at position 192 in SEQ ID NO: 1), corresponding to the extracellular domain of the wild-type human FcγRIIIa (the EC domain in FIG. 1) of the amino acid sequence of Fc-binding protein comprising the amino acid sequence listed as SEQ ID NO: 4, wherein the protein having an amino acid substitution at least at a specific position among the amino acid residues from position 33 to position 208. Thus, the Fc-binding protein of the invention may include all or a portion of the signal peptide region (S in FIG. 1) at the N-terminal end of the extracellular domain, or it may include all or a portion of the cell membrane-spanning region (TM in FIG. 1) at the C-terminal end of the extracellular domain, and the intracellular domain (C in FIG. 1). The amino acid substitution at the specific position is, specifically, Glu37Gly (which means that the glutamic acid at position 37 of SEQ ID NO: 4 is replaced by glycine, same hereunder), Leu39Met, Val43Glu, Phe45Ile, Gln49Pro, Tyr51Asn, Lys56Gln, Gln64Arg, Tyr67His, Glu70Asp, Asn72Asp, Ser81Arg, Ser84Pro, Tyr90Phe, Phe91Ile, Ala94Ser, Thr96Ser, Asn108Ser, Val133Glu, Lys135Val, Glu137Gly, Asp138Glu, Lys148Arg, Thr156Met, Tyr157Phe, Gly163Val, Tyr174Val, Lys181Glu, Phe187Ser, Ser194Arg, Asn196Lys, Glu200Gly, Thr201Ala, Asn203Asp and Ile206Val.

The Fc-binding protein of the invention only needs to have at least the amino acid substitutions at the aforementioned specific positions, and so long as it has antibody-binding activity it may also have one or more other substitutions, deletions, insertions or additions of amino acid residues. Specific examples of this aspect include Fc-binding proteins with antibody-binding activity, according to the following (i) to (v):

(i) An Fc-binding protein comprising amino acid residues from glycine at position 33 to glutamine at position 208 in the amino acid sequence listed as SEQ ID NO: 4, but has amino acid substitutions at the aforementioned specific positions, and further has at least the amino acid substitutions Val192Ile, Val192Ala and Val192Tyr;

(ii) An Fc-binding protein comprising the amino acid residues from glycine at position 33 to glutamine at position 208 in the amino acid sequence listed as SEQ ID NO: 4, but has amino acid substitutions at the aforementioned specific positions, and further has one or more substitutions, deletions, insertions or additions of one or more amino acid residues other than the amino acid substitutions at the aforementioned specific positions;

(iii) An Fc-binding protein comprising the amino acid residues from glycine at position 33 to glutamine at position 208 in the amino acid sequence listed as SEQ ID NO: 4, but has amino acid substitutions at the aforementioned specific positions, further has one or more substitutions, deletions, insertions or additions of one or more amino acid residues other than the amino acid substitutions at the aforementioned specific positions, and further has the amino acid substitution Val192Ile, Val192Ala or Val192Tyr;

(iv) An Fc-binding protein having an amino acid sequence having at least 70% homology with an amino acid sequence comprising amino acid residues from glycine at position 33 to glutamine at position 208 of the amino acid sequence listed as SEQ ID NO: 4, and further has the amino acid substitutions at the aforementioned specific positions;

(v) An Fc-binding protein having an amino acid sequence having at least 70% homology with an amino acid sequence comprising amino acid residues from glycine at position 33 to glutamine at position 208 of the amino acid sequence listed as SEQ ID NO: 4, and further has the amino acid substitutions at the aforementioned specific positions and the amino acid substitution Val192Ile, Val192Ala or Val192Tyr;

(vi) An Fc-binding protein having amino acid substitutions at the aforementioned specific positions in an amino acid sequence having at least 70% homology with an amino acid sequence comprising amino acid residues from glycine at position 33 to glutamine at position 208 of the amino acid sequence listed as SEQ ID NO: 4;

(vii) An Fc-binding protein having the amino acid substitutions at the aforementioned specific positions and the amino acid substitution Val192Ile, Val192Ala or Val192Tyr, in an amino acid sequence having at least 70% homology with an amino acid sequence comprising amino acid residues from glycine at position 33 to glutamine at position 208 of the amino acid sequence listed as SEQ ID NO: 4.

The amino acid substitution Val192Ile, Val192Ala or Val192Tyr mentioned in (i), (iii), (v) and (vii) above is an amino acid substitution that increases productivity in transformants. Therefore, if the Fc-binding protein of the invention having at least the amino acid substitutions at the aforementioned specific positions also has the other amino acid substitutions mentioned above, then an Fc-binding protein with higher alkali resistance than the wild-type FcγRIIIa and greater productivity by transformants can be obtained.

Throughout the present specification, the "substitution, deletion, insertion or addition of one or more amino acid residues" and the "one or more of substitutions, deletions, insertions or additions of amino acid residues", may be a substitution, deletion, insertion or addition of 1 to 50 amino acid residues, for example, but it is preferably a substitution, deletion, insertion or addition of preferably 1 to 40, more preferably 1 to 30, even more preferably 1 to 20 (1, 2, 3, 4, 5, 6, 7, 8, 9, 10, 11, 12, 13, 14, 15, 16, 17, 18, 19 or 20) and most preferably 1 to 10 (1, 2, 3, 4, 5, 6, 7, 8, 9 or 10) amino acid residues, although this will differ depending on the positions of the amino acid residues in the spatial configuration of the protein, and the types of amino acid residues. Moreover, the terms "substitution", "deletion", "insertion" and "addition" as used herein include naturally occurring mutations which are individual differences between microorganisms and differences between species from which the gene is derived (mutants or variants). Human FcγRIIIa is also known to have amino acid-substituted forms with one or more amino acid substitutions from among Leu82His, Leu82Arg, Gly163Asp and Tyr174His, and the Fc-binding protein of the invention may also include these amino acid substitutions.

The amino acid sequence homology of (iv) and (v) above may be 70% or higher, 71% or higher, 72% or higher, 73% or higher, 74% or higher, 75% or higher, 76% or higher, 77% or higher, 78% or higher, 79% or higher or 80% or higher.

The amino acid sequence homology of (vi) and (vii) above may be 70% or higher, 71% or higher, 72% or higher, 73% or higher, 74% or higher, 75% or higher, 76% or higher, 77% or higher, 78% or higher, or 79% or higher, preferably 80% or higher, 81% or higher, 82% or higher, 83% or higher or 84% or higher, more preferably 85% or higher, 86% or higher, 87% or higher, 88% or higher or 89% or higher, and even more preferably 90% or higher, 91% or higher, 92% or higher, 93% or higher, 94% or higher, 95% or higher, 96% or higher, 97% or higher, 98% or higher or 99% or higher.

As used herein, "homology" of an amino acid sequence has the same definition as the "identity" of the amino acid sequence. The "identity (homology)" of an amino acid sequence is determined by aligning two amino acid sequences to be compared so that the maximum number of amino acid residues match, and expressing the number of matching amino acid residues as a percentage with respect to the total number of amino acid residues. During alignment, gaps may be appropriately inserted as necessary in either or both of the two sequences being compared. The method of aligning the sequences is not particularly restricted, and it may be carried out using a known sequence comparison program such as BLAST, FASTA or CLUSTAL W. When gaps are inserted, the total number of amino acid residues is the number of residues with each gap being counted as a single amino acid residue. When the total numbers of amino acid residues counted in this manner differ between the two sequences, the sequence identity (%) is calculated by dividing the number of matching amino acid residues by the total number of amino acid residues of the longer sequence.

The Fc-binding protein of the invention may also have a conservative substitution which is a substitution between amino acids which are similar in either or both the physical and chemical properties of the amino acids. It is known to those skilled in the art that with a conservative substitution, protein function is maintained between proteins with the substitution and proteins without the substitution, as a general rule which is not limited to Fc-binding protein. Examples of conservative substitutions include substitutions between glycine and alanine, aspartic acid and glutamic acid, serine and proline or glutamic acid and alanine (Tanpakushitsu no Kozou to Kinou, Medical Science International, 9, 2005).

A oligopeptide useful for isolating the target antibody from solution in the presence of contaminants may also be added at the N-terminal end or C-terminal end of the Fc-binding protein of the invention. Such oligopeptides include polyhistidine, polylysine, polyarginine, polyglutamic acid and polyaspartic acid. In addition, a cysteine-including oligopeptide, which is useful for immobilizing the Fc-binding protein of the invention on a solid phase such as a chromatography support, may also be added to the N-terminal end or C-terminal end of the Fc-binding protein of the invention. There is no particular restriction on the length of the oligopeptide to be added to the N-terminal end or C-terminal end of the Fc-binding protein. When the oligopeptide is to be added to the Fc-binding protein of the invention, first a polynucleotide encoding the oligopeptide may be prepared and then added by genetic engineering to the N-terminal end or C-terminal end of the Fc-binding protein by a method known to those skilled in the art, or the chemically synthesized oligopeptide may be chemically bonded to the N-terminal end or C-terminal end of the Fc-binding protein of the invention. Alternatively, a signal peptide that promotes efficient host expression may be added to the N-terminal end of the Fc-binding protein of the invention as the ligand of the adsorbent. Examples for the signal peptide, when the host is *E. coli*, include signal peptides that secrete proteins in the periplasm, such as PelB, DsbA, MalE (the region from position 1 to position 26 of the amino acid sequence listed as UniProt No. POAEX9) or TorT (Japanese Unexamined Patent Publication No. 2011-097898).

A preferred mode of the Fc-binding protein of the invention is an Fc-binding protein comprising a polypeptide consisting of the amino acid sequence represented by the following (a), (b) or (c). These Fc-binding proteins are preferred from the viewpoint of increasing the stability against alkalis (alkali resistance).

(a) FcR35d (the amino acid residues from position 33 to position 208 of the amino acid sequence listed as SEQ ID NO: 7)

A polypeptide having the amino acid residues from glycine at position 33 to glutamine at position 208 in the amino acid sequence listed as SEQ ID NO: 4, but having the amino acid substitutions Glu37Gly, Leu39Met, Val43Glu, Phe45Ile, Gln49Pro, Tyr51Asn, Lys56Gln, Gln64Arg, Tyr67His, Glu70Asp, Asn72Asp, Ser81Arg, Ser84Pro, Tyr90Phe, Phe91Ile, Ala94Ser, Thr96Ser, Asn108Ser, Val133Glu, Lys135Val, Glu137Gly, Asp138Glu, Lys148Arg, Thr156Met, Tyr157Phe, Gly163Val, Tyr174Val, Lys181Glu, Phe187Ser, Ser194Arg, Asn196Lys, Glu200Gly, Thr201Ala, Asn203Asp and Ile206Val in the amino acid residues from position 33 to position 208.

(b) FcR36i (the amino acid residues from position 33 to position 208 of the amino acid sequence listed as SEQ ID NO: 9)

A polypeptide having the amino acid residues from glycine at position 33 to glutamine at position 208 in the amino acid sequence listed as SEQ ID NO: 4, but having the amino acid substitutions Glu37Gly, Leu39Met, Val43Glu, Phe45Ile, Gln49Pro, Tyr51Asn, Lys56Gln, Gln64Arg, Tyr67His, Glu70Asp, Asn72Asp, Ser81Arg, Ser84Pro, Tyr90Phe, Phe91Ile, Ala94Ser, Thr96Ser, Asn108Ser, Val133Glu, Lys135Val, Glu137Gly, Asp138Glu, Lys148Arg, Thr156Met, Tyr157Phe, Gly163Val, Tyr174Val, Lys181Glu, Phe187Ser, Val192Ile, Ser194Arg, Asn196Lys, Glu200Gly, Thr201Ala, Asn203Asp and Ile206Val in the amino acid residues from position 33 to position 208.

(c) FcR36a (the amino acid residues from position 33 to position 208 of the amino acid sequence listed as SEQ ID NO: 11)

A polypeptide having the amino acid residues from glycine at position 33 to glutamine at position 208 in the amino acid sequence listed as SEQ ID NO: 4, but having the amino acid substitutions Glu37Gly, Leu39Met, Val43Glu, Phe45Ile, Gln49Pro, Tyr51Asn, Lys56Gln, Gln64Arg, Tyr67His, Glu70Asp, Asn72Asp, Ser81Arg, Ser84Pro, Tyr90Phe, Phe91Ile, Ala94Ser, Thr96Ser, Asn108Ser, Val133Glu, Lys135Val, Glu137Gly, Asp138Glu, Lys148Arg, Thr156Met, Tyr157Phe, Gly163Val, Tyr174Val, Lys181Glu, Phe187Ser, Val192Ala, Ser194Arg, Asn196Lys, Glu200Gly, Thr201Ala, Asn203Asp and Ile206Val in the amino acid residues from position 33 to position 208.

Of the Fc-binding proteins listed as SEQ ID NO: 7, 9 and 11, the region from methionine at position 1 to alanine at position 26 is the MalE signal peptide, the region from lysine at position 27 to methionine at position 32 is a linker sequence, the region from glycine at position 33 to glutamine at position 208 is the amino acid sequence of a polypeptide capable of binding to the Fc region of an antibody (FcR35d (SEQ ID NO: 7), FcR36i (SEQ ID NO: 9) or FcR36a (SEQ ID NO: 11)), the region of glycine from position 209 to position 210 is a linker sequence, and the region of histidine from position 211 to position 216 is the tag sequence.

Examples of methods for preparing a polynucleotide encoding the Fc-binding protein of the invention (hereunder also referred to simply as "polynucleotide of the invention") include:

(I) a method in which the amino acid sequence of the Fc-binding protein of the invention is converted to a nucleotide sequence, and a polynucleotide comprising that nucleotide sequence is artificially synthesized, and (II) a method in which polynucleotides encoding the full or partial sequence for the Fc-binding protein are prepared directly in an artificial manner, or are prepared by a DNA amplification method such as PCR from cDNA for the Fc-binding protein, and the prepared polynucleotides are linked by an appropriate method.

In the method of (I), during conversion from the amino acid sequence to the nucleotide sequence, the frequency of codon usage in the host to be transformed is preferably considered for the conversion. As an example, when the host is E. coli (Escherichia coli), the usage frequencies of AGA/AGG/CGG/CGA for arginine (Arg), ATA for isoleucine (Ile), CTA for leucine (Leu), GGA for glycine (Gly) and CCC for proline (Pro) are low (being rare codons), and therefore the conversion may be carried out in a manner that avoids these codons. Analysis of the codon usage frequencies may be accomplished utilizing a public database (for example, the Codon Usage Database found on the home page of the Kazusa DNA Research Institute).

An error-prone PCR method may be used for introduction of a mutation into a polynucleotide of the invention. The reaction conditions for the error-prone PCR method are not particularly restricted so long as they are conditions allowing introduction of the desired mutation into a polynucleotide encoding Fc-binding protein, and for example, a mutation may be introduced into the polynucleotide by PCR in which non-homogeneous concentrations of the four different deoxynucleotides (dATP/dTTP/dCTP/dGTP) as substrates are prepared, and $MnCl_2$ is added to the PCR reaction mixture at concentrations from 0.01 to 10 mM (preferably 0.1 to 1 mM). As methods of mutagenesis other than error-prone PCR, there may be mentioned methods in which a polynucleotide comprising the full or partial sequence of Fc-binding protein is contacted with and acted on by a chemical agent that acts as a mutagen, or is irradiated with ultraviolet rays, to introduce mutations into the polynucleotide. In such methods, the chemical agent used as the mutagen may be a mutagenic chemical agent that is commonly used by those skilled in the art, such as hydroxylamine, N-methyl-N'-nitro-N-nitrosoguanidine, nitrous acid, sulfurous acid or hydrazine.

There are no particular restrictions on the host that is to express the Fc-binding protein of the invention, and examples include animal cells (CHO (Chinese Hamster Ovary) cells, HEK cells, Hela cells, COS cells and the like), yeast (*Saccharomyces cerevisiae, Pichia pastoris, Hansenula polymorpha, Schizosaccharomyces japonicus, Schizosaccharomyces octosporus, Schizosaccharomyces pombe* and the like), insect cells (Sf9, Sf21 and the like), *E. coli* (JM109, BL21(DE3), W3110 and the like), and *Bacillus subtilis*. Animal cells and *E. coli* are generally preferred as the host from the standpoint of productivity, with *E. coli* being more preferred as the host.

When a polynucleotide of the invention is used for transformation of a host, the polynucleotide of the invention itself may be used, but it is more preferred to use a polynucleotide of the invention having an expression vector (for example, bacteriophage, cosmids, plasmids or the like that are commonly used for transformation of prokaryotic cells or eukaryotic cells) inserted at an appropriate location. The expression vector is not particularly restricted so long as it is stably present and can replicate in the host to be transformed, and when *E. coli* is used as the host, examples include pET plasmid vector, pUC plasmid vector, pTrc plasmid vector, pCDF plasmid vector and pBBR plasmid vector. The "appropriate location" is a location where the replicating function of the expression vector, the desired antibiotic marker and the transfer-associated regions are not destroyed. When a polynucleotide of the invention is to be inserted in the expression vector, it is preferably inserted in a manner linked to a functional polynucleotide such as a promoter, which is necessary for expression. Examples of such promoters include, for *E. coli* as the host, trp promoter, tac promoter, trc promoter, lac promoter, T7 promoter, recA promoter and lpp promoter, as well as the λ phage λPL promoter and λPR promoter, and for animal cells as the host, SV40 promoter, CMV promoter and CAG promoter.

Transformation of the host using an expression vector in which the polynucleotide of the invention has been inserted (hereunder referred to as "expression vector of the invention"), prepared in the manner described above, can be accomplished by a method commonly employed by those skilled in the art. For example, when selecting a microorganism belonging to the genus *Escherichia* (*E. coli* JM109,

*E. coli* BL21(DE3), *E. coli* W3110 or the like) as the host, the transformation may be carried out by a method described in the known literature (for example, Molecular Cloning, Cold Spring Harbor Laboratory, 256, 1992). Electroporation or lipofection may be used when the host cells are animal cells. The transformants produced by transformation by such a method can be obtained by screening by an appropriate method to obtain transformants capable of expressing the Fc-binding protein of the invention (hereunder referred to as "transformants of the invention").

For preparation of an expression vector of the invention from transformants of the invention, the expression vector of the invention may be extracted from the transformants of the invention by a method suited for the host used for transformation. When the hosts for the transformants of the invention are *E. coli*, they may be prepared from a cultured product obtained by culturing the transformants, using an alkaline extraction method or a commercially available extraction kit such as a QIAprep Spin Miniprep kit (product of Qiagen Inc.).

By culturing the transformants of the invention and recovering the Fc-binding protein of the invention from the obtained cultured product, it is possible to produce an Fc-binding protein of the invention. Throughout the present specification, the term "cultured product" includes the cultured cells of the transformants of the invention themselves, as well as the culture medium used for culturing. The transformants used in the method for producing a protein according to the invention may be cultured in medium suitable for culturing of the host, and when the host is *E. coli*, LB (Luria-Bertani) culture medium, supplemented with necessary nutrients, may be mentioned as a preferred medium. In order to selectively grow the transformants of the invention based on whether the expression vector of the invention has been introduced, preferably a chemical agent for a drug resistance gene present in the vector is added to the medium and culturing is performed. For example, when the vector includes a kanamycin resistance gene, kanamycin may be added to the culture medium. There may also be added to the culture medium, in addition to carbon, nitrogen and inorganic salt sources, various appropriate nutrients, and optionally one or more different reducing agents selected from the group consisting of glutathione, cysteine, cystamine, thioglycolate and dithiothreitol.

There may also be added reagents that promote protein secretion from the transformants into the culture solution, such as glycine, and specifically when the host is *E. coli*, glycine is preferably added at no greater than 2% (w/v) to the culture medium. When the host is *E. coli*, the culturing temperature will generally be 10° C. to 40° C., preferably 20° C. to 37° C. and more preferably around 25° C., although this may be selected depending on the properties of the protein to be expressed. The pH of the culture medium is from pH 6.8 to pH 7.4 and preferably around pH 7.0, when the host is *E. coli*. When an inducible promoter is included in the vector of the invention, it is preferably induced under conditions such that the Fc-binding protein of the invention can be satisfactorily expressed. The inducing agent may be IPTG (isopropyl-β-D-thiogalactopyranoside), for example. When the host is *E. coli*, the turbidity of the culture solution is measured (at an absorbance of 600 nm), a suitable amount of IPTG is added when the value reaches about 0.5 to 1.0, and then culturing is continued, thereby allowing expression of the Fc-binding protein to be induced. The concentration of the IPTG added may be appropriately selected in the range of 0.005 to 1.0 mM, and preferably in the range of 0.01 to 0.5 mM. The various conditions for IPTG induction may be known conditions in the technical field.

For recovery of the Fc-binding protein of the invention from the cultured product obtained by culturing the transformants of the invention, the Fc-binding protein of the invention may be recovered by isolation and purification from the cultured product by a method suited for the form of expression of the Fc-binding protein of the invention in the transformants of the invention. For example, in the case of expression in culture supernatant, the cells may be isolated by centrifugal separation and the Fc-binding protein of the invention purified from the obtained culture supernatant. When the expression is intracellular (including the periplasm), the cells may be collected by centrifugal separation, and then an enzyme treatment agent, surfactant or the like may be added or ultrasonic waves or a French press may be used to disrupt the cells, after which the Fc-binding protein of the invention may be extracted and purified. A method known in the technical field may be used for purification of the Fc-binding protein of the invention, an example of which is isolation/purification using liquid chromatography. Liquid chromatography includes ion-exchange chromatography, hydrophobic interaction chromatography, gel filtration chromatography and affinity chromatography, and these chromatography methods may also be combined for purification to prepare a high-purity Fc-binding protein of the invention.

The method of measuring the binding activity of the obtained Fc-binding protein of the invention for IgG may be, for example, measurement of the binding activity for IgG using Enzyme-Linked ImmunoSorbent Assay (hereunder, ELISA), a surface plasmon resonance method, or similar. When a modified form of human Fc-binding protein is used, the IgG used for measurement of binding activity is preferably human IgG and most preferably human IgG1 or human IgG3.

An adsorbent of the invention can be produced by immobilizing the Fc-binding protein of the invention to an insoluble support. There are no particular restrictions on the insoluble support, and examples include supports where the starting material is a polysaccharide such as agarose, alginate, carrageenan, chitin, cellulose, dextrin, dextran or starch, supports where the starting material is a synthetic polymer such as polyvinyl alcohol, polymethacrylate, poly (2-hydroxyethyl methacrylate) or polyurethane, and supports where the starting material is a ceramic such as silica. Preferred among these as the insoluble support are supports where the starting material is a polysaccharide and supports where the starting material is a synthetic polymer. Examples of preferred supports include hydroxyl-introduced polymethacrylate gels such as Toyopearl (by Tosoh Corp.), agarose gels such as Sepharose (by GE Healthcare), and cellulose gels such as CELLUFINE (by JNC). There are no particular restrictions on the form of the insoluble support, and it may be granular, non-granular, porous or non-porous.

For immobilization of the Fc-binding protein on the insoluble support, the insoluble support may be provided with active groups such as N-hydroxysuccinic acid imide (NHS) activated ester groups, epoxy, carboxyl, maleimide, haloacetyl, tresyl, formyl and haloacetamide groups, the immobilization being accomplished by covalent bonding between the human Fc-binding protein and insoluble support through the active groups. The support with the active groups may be a commercially available support used as is, or it may be prepared by introducing active groups onto the support surface under appropriate reaction conditions. Examples of commercially available supports with active groups include TOYOPEARL AF-Epoxy-650M and TOYO- PEARL AF-Tresyl-650M (both by Tosoh Corp.), HiTrap NHS-activated HP Columns, NHS-activated Sepharose 4 Fast Flow and Epoxy-activated Sepharose 6B (all by GE Healthcare), and SulfoLink Coupling Resin (by Thermo Scientific).

Examples of methods for introducing active groups onto the support surface, on the other hand, include methods in which one site of a compound with two or more active sites is reacted with hydroxyl, epoxy, carboxyl and amino groups present on the support surface. Compounds having epoxy groups introduced onto hydroxyl or amino groups on the support surface, as examples of such compounds, include epichlorhydrin, ethanediol diglycidyl ether, butanediol diglycidyl ether and hexanediol diglycidyl ether. Compounds that introduce carboxyl groups onto the support surface after epoxy groups have been introduced onto the support surface by the compounds, include 2-mercaptoacetic acid, 3-mercaptopropionic acid, 4-mercaptobutyric acid, 6-mercaptobutyric acid, glycine, 3-aminopropionic acid, 4-aminobutyric acid and 6-aminohexanoic acid.

Examples of compounds that introduce maleimide groups onto hydroxyl or epoxy, carboxyl or amino groups present on the support surface include N-(ε-maleimidecaproic acid) hydrazide, N-(ε-maleimidepropionic acid)hydrazide, 4-[4-N-maleimidephenyl]acetic acid hydrazide, 2-aminomaleimide, 3-aminomaleimide, 4-aminomaleimide, 6-aminomaleimide, 1-(4-aminophenyl)maleimide, 1-(3-aminophenyl)maleimide, 4-(maleimide)phenylisocyanato, 2-maleimideacetic acid, 3-maleimidepropionic acid, 4-maleimidebutyric acid, 6-maleimidehexanoic acid, (N-[α-maleimideacetoxy] succinimide ester), (m-maleimidebenzoyl)N-hydroxysuccinimide ester, (succinimidyl-4-[maleimidemethyl]cyclohexane-1-carbonyl-[6-aminohexanoic acid]), (succinimidyl-4-[maleimidemethyl] cyclohexane-1-carboxylic acid), (p-maleimidebenzoyl)N-hydroxysuccinimide ester and (m-maleimidebenzoyl)N-hydroxysuccinimide ester.

Examples of compounds that introduce haloacetyl groups onto hydroxyl or amino groups present on the support surface include chloroacetic acid, bromoacetic acid, iodoacetic acid, chloroacetic acid chloride, bromoacetic acid chloride, bromoacetic acid bromide, chloroacetic anhydride, bromoacetic anhydride, iodoacetic anhydride, 2-(iodoacetamide)acetic acid-N-hydroxysuccinimide ester, 3-(bromoacetamide)propionic acid-N-hydroxysuccinimide ester and 4-(iodoacetyl)aminobenzoic acid-N-hydroxysuccinimide ester. There may also be mentioned methods in which an ω-alkenylalkaneglycidyl ether is reacted with hydroxyl or amino groups present on the support surface, and then the ω-alkenyl site is halogenated with a halogenating agent and activated. Examples of ω-alkenylalkaneglycidyl ethers include allyl glycidyl ether, 3-butenyl glycidyl ether and 4-pentenyl glycidyl ether, and examples of halogenating agents include N-chlorosuccinimide, N-bromosuccinimide and N-iodosuccinimide.

A different example of a method for introducing active groups onto the support surface, is a method in which activated groups are introduced onto the carboxyl groups present on the support surface, using a condensation agent and an additive. Examples of condensation agents include 1-ethyl-3-(3-dimethylaminopropyl)carbodiimide (EDC), dicyclohexylcarbodiamide and carbonyldiimidazole. Examples of additives include N-hydroxysuccinic acid imide (NHS), 4-nitrophenol and 1-hydroxybenzotriazole.

The buffer to be used for immobilization of the Fc-binding protein of the invention on the insoluble support may be acetate buffer, phosphate buffer, MES (2-MorpholinoEthaneSulfonic acid) buffer, HEPES (4-(2-HydroxyEthyl)-1-PiperazineEthaneSulfonic acid) buffer, Tris buffer or borate buffer. The reaction temperature for immobilization may be appropriately set in a temperature range from 5° C. to 50° C., and is preferably in the range of 10° C. to 35° C., from the viewpoint of the reactivity of the active groups and the stability of the Fc-binding protein of the invention.

For isolation of an antibody using an adsorbent of the invention obtained by immobilizing the Fc-binding protein of the invention on an insoluble support, for example, a buffering solution containing an antibody may be added to a column packed with an adsorbent of the invention, using delivery means such as a pump, specifically adsorbing the antibody onto the adsorbent of the invention, and then a suitable eluent may be added to the column to elute the antibody. Incidentally, before adding the buffering solution containing the antibody with sugar chains to the column, the column is preferably equilibrated using an appropriate buffering solution to allow isolation of the antibody to a higher purity. Examples for the buffering solution include buffering solutions with inorganic salts as components, such as phosphate buffer. The pH of the buffer is pH 3 to 10 and preferably pH 4 to 8. For elution of the antibody that has been adsorbed onto the adsorbent of the invention, it is sufficient to weaken the interaction between the antibody with sugar chains and the ligand (the Fc-binding protein of the invention), and specifically, this may be by changing the pH with the buffering solution, or using a counter peptide, changing the temperature or changing the salt concentration. A specific example of an eluent for elution of the antibody that has been adsorbed on the adsorbent of the invention is a buffering solution that is more toward the acidic end than the solution used for adsorption of the antibody onto the adsorbent of the invention. Examples of types of buffering solutions include citrate buffer, glycine hydrochloride buffer and acetate buffer, having buffer capacity at the acidic end. The pH of the buffering solution may be set within a range that does not impair the function of the antibody, and it is preferably pH 2.5 to 6.0, more preferably pH 3.0 to 5.0 and even more preferably pH 3.0 to 4.0.

When the antibody is to be eluted by varying the salt concentration, it may be eluted in a single step with a buffer (eluent) containing a salt at high concentration, or the salt concentration may optionally be increased in stages (step gradient), or the salt concentration may be increased with a linear concentration gradient (linear gradient), but preferably elution is performed with a linear gradient. For example, when sodium chloride is used as a water-soluble salt, elution may be performed with a linear gradient from 0 M to 1 M concentration of sodium chloride. When the antibody is to be eluted by varying the pH, it may be eluted in a single step with an acidic buffer (eluent) having the pH lowered with an equilibrating buffer, or the pH of the buffer may optionally be lowered in steps (step gradient), or the pH of the buffer may be lowered with a linear concentration gradient (linear gradient), but preferably elution is performed with a linear gradient. For example, elution may be performed with a linear gradient, from a neutral to weakly acidic buffer in which the antibody is adsorbed, to an acidic buffer in which the antibody is eluted.

The fraction containing the antibody which has been eluted by the method described above may be fractionated to obtain the antibody. The fractionation may be carried out by a common method. Specific examples are a method of exchanging the collecting container at fixed periods of time or at fixed volumes, or exchanging the collecting container according to the shape of the chromatogram of the eluent, or separating off the fraction with an automatic fraction collector.

When an antibody is to be isolated from the antibody-containing solution using the adsorbent of the invention, since the Fc-binding protein of the invention recognizes differences in sugar chain structures bonded to the antibody, the antibody will successively elute based on differences in sugar chain structures of the antibody, and therefore it is preferred to use an elution liquid with different antibody elution positions (elution fractions). By thus separating the antibodies using an adsorbent of the invention it is possible to identify differences in sugar chain structures of antibodies. There are no particular restrictions on the structures of sugar chains that can be identified, and as examples, there may be mentioned sugar chains added when expressing antibodies in animal cells such as CHO cells, or yeast such as *Pichia* yeast or *Saccharomyces* yeast, as the host, sugar chains on human antibodies, or sugar chains added to antibodies by chemical synthesis methods. The adsorbent of the invention can isolate the antibody based on differences in the sugar chain structures of the antibody.

Advantageous Effects of Invention

The Fc-binding protein of the invention has excellent stability against alkalis (alkali resistance) compared to the wild-type Fc-binding protein. When the Fc-binding protein of the invention is to be used as an affinity ligand for an antibody adsorbent, it is possible to obtain an adsorbent with high stability (resistance) against alkali cleaning. It can therefore contribute to cost reduction for industrial production of antibody drugs.

Moreover, it is possible to further improve productivity by transformants if amino acid residues at specific positions of the Fc-binding protein of the invention are replaced by other specific amino acid residues.

BRIEF DESCRIPTION OF DRAWINGS

FIG. 1 is a schematic diagram of human FcγRIIIa. The numerals in the diagram represent the amino acid sequence positions in SEQ ID NO: 1. Also in the diagram, S represents the signal sequence, EC represents the extracellular domain, TM represents the cell membrane-spanning region and C represents the intracellular region.

FIG. 2 is a chromatogram obtained upon separating a monoclonal antibody (Rituxan) with FcR36i-immobilized gel. Rituxan was eluted using 20 mM acetate buffer (pH 4.8) and 10 mM glycine hydrochloride buffer (pH 3.0), by linear gradient elution with the 10 mM glycine hydrochloride buffer (pH 3.0) at 0% to 100%.

EXAMPLES

Figure 3:
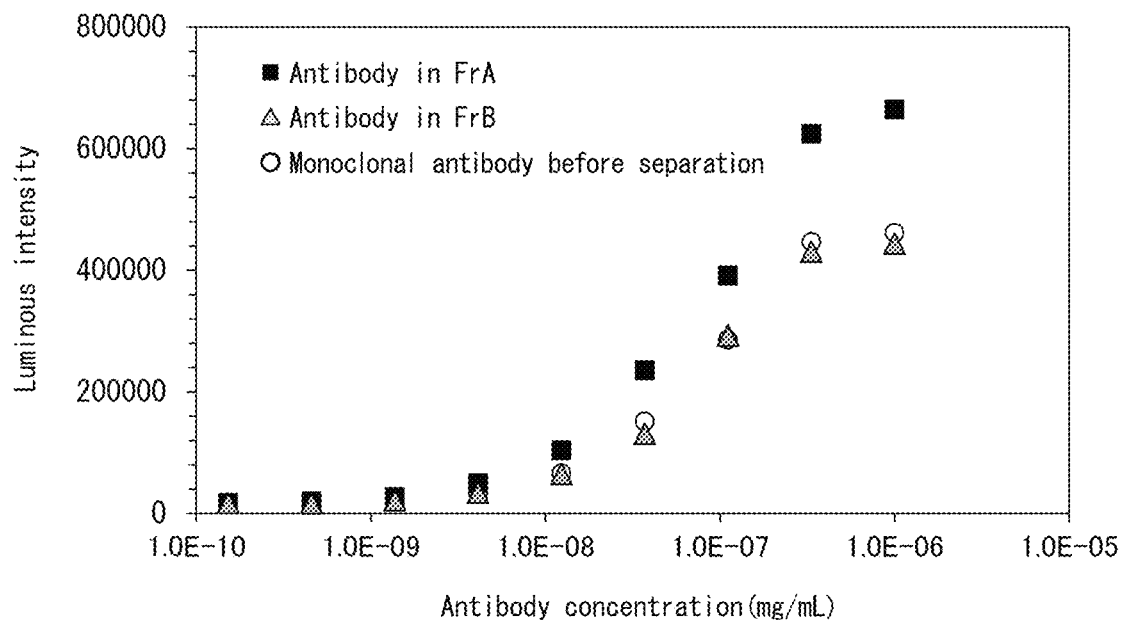
FIG. 3 shows the results of measuring ADCC activity of a monoclonal antibody (Rituxan) separated by linear gradient elution using FcR36i-immobilized gel.

The present invention will now be described in greater detail by examples, with the understanding that the invention is not limited to the examples.

Example 1 Mutagenesis in Fc-Binding Protein and Construction of Library

Random mutagenesis by error-prone PCR was carried out on a polynucleotide encoding FcR35c-containing Fc-binding protein (SEQ ID NO: 5), prepared by the method described in Japanese Unexamined Patent Publication No. 2017-118871. Incidentally, FcR35c (the amino acid residues from position 33 to position 208 of the amino acid sequence listed as SEQ ID NO: 5) is a polypeptide having the amino acid residues from glycine at position 33 to glutamine at position 208 of SEQ ID NO: 4 (from glycine at position 17 to glutamine at position 192 in SEQ ID NO: 1), corresponding to the extracellular domain of the wild-type human FcγRIIIa (the EC domain in FIG. 1), but having the amino acid substitutions Glu37Gly (which means that the glutamic acid at position 37 of SEQ ID NO: 4 is replaced by glycine, same hereunder), Leu39Met, Val43Glu, Phe45Ile, Gln49Pro, Tyr51Asn, Lys56Gln, Gln64Arg, Tyr67His, Glu70Asp, Asn72Asp, Ser84Pro, Tyr90Phe, Phe91Ile, Ala94Ser, Thr96Ser, Asp98Glu, Asn108Ser, Asp114Glu, Gln117 Leu, Val133Glu, Lys135Val, Glu137Gly, Asp138Glu, Lys148Arg, Thr156Met, Tyr157Phe, Gly163Val, Tyr174Val, Lys181Glu, Phe187Ser, Ser194Arg, Thr201Ala, Asn203Glu, Ile206Val and Gln208Pro among the amino acid residues from position 33 to position 208.

(1) Error-prone PCR was carried out using expression vector pET-FcR35c prepared by the method described in Japanese Unexamined Patent Publication No. 2017-118871 as the template (the sequence of the polynucleotide encoding Fc-binding protein listed as SEQ ID NO: 5 in this expression vector is shown as SEQ ID NO: 6). The error-prone PCR was carried out by preparing a reaction mixture with the composition shown in Table 1, and then heat treating the reaction mixture at 95° C. for 2 minutes, carrying out 35 cycles of reaction where one cycle consisted of a first step at 95° C. for 30 seconds, a second step at 60° C. for 30 seconds and a third step at 72° C. for 90 seconds, and finally conducting heat treatment at 72° C. for 7 minutes. As a result of the reaction, mutations were satisfactorily introduced into the polynucleotide encoding Fc-binding protein.

TABLE 1

| Composition | Volume |
| --- | --- |
| Template DNA (pET-FcR35c, concentration: 12 ng/μL) | 1 μL |
| 10 μM PCR primer (SEQ ID NO: 2) | 4 μL |
| 10 μM PCR primer (SEQ ID NO: 3) | 4 μL |
| 2.5 mM MgCl$_2$ | 12 μL |
| 10 mM dATP | 2 μL |
| 10 mM dGTP | 2 μL |
| 10 mM dCTP | 10 μL |
| 10 mM dTTP | 10 μL |
| 10 mM MnCl$_2$ | 4 μL |
| 10 × Ex Taq Buffer (Takara Bio, Inc.) | 10 μL |

TABLE 1-continued

| Composition | Volume |
|---|---|
| GoTaq polymerase (Promega) | 1 μL |
| H₂O | up to 100 μL |

(2) After purifying the PCR product obtained in (1), it was digested with restriction enzymes NcoI and HindIII, and ligated with expression vector pETMalE previously digested with the same restriction enzymes (Japanese Unexamined Patent Publication No. 2011-206046).

(3) Upon completion of the ligation reaction, the reaction mixture was introduced into *E. coli* BL21(DE3) by electroporation, and culturing was conducted on LB plate culture medium containing 50 μg/mL kanamycin, after which the colonies formed on the plate were used as a random mutation library.

Example 2: Screening of Fc-Binding Protein with Alkali Resistance (1) The random mutation library (of transformants) prepared in Example 1 was inoculated into 200 μL of 2YT liquid medium (16 g/L peptone, 10 g/L yeast extract, 5 g/L sodium chloride) containing 50 μg/mL kanamycin, and a 96-well deep well plate was used for shake culturing overnight at 30° C.

(2) After culturing, 5 μL of culture solution was subcultured on 2YT liquid medium containing 500 μL of 0.05 mM IPTG (isopropyl-β-D-thiogalactopyranoside), 0.3% (w/v) glycine and 50 μg/mL kanamycin, and a 96-well deep well plate was used for shake culturing overnight at 20° C.

(3) After culturing, the culture supernatant containing the Fc-binding protein obtained by centrifugation was diluted 25-fold with purified water and mixed with an equivalent amount of 500 mM sodium hydroxide, and then allowed to stand at 30° C. for 3 hours for alkali treatment. After alkali treatment, the pH was adjusted to near neutral with a 4-fold amount of 1 M Tris buffer (pH 7.0).

(4) The antibody-binding activity of the Fc-binding protein after the alkali treatment of (3) and the antibody-binding activity of the Fc-binding protein without the alkali treatment of (3) were each measured by the ELISA method described below, and the antibody-binding activity of the Fc-binding protein after alkali treatment was divided by the antibody-binding activity of the Fc-binding protein without alkali treatment to calculate the residual activity.

(4-1) A gammaglobulin preparation (by Kaketsuken) as the human antibody, was immobilized in the wells of a 96-well microplate at 1 μg/well (at 4° C. for 18 hours), and after complete immobilization, blocking was performed with 20 mM Tris-HCl buffering solution (pH 7.4) containing 2% (w/v) SKIM MILK (product of BD Co.) and 150 mM sodium chloride.

(4-2) After rinsing with wash buffer (20 mM Tris-HCl buffer (pH 7.4) containing 0.05% [w/v] Tween 20 and 150 mM NaCl), a solution containing Fc-binding protein for evaluation of the antibody-binding activity was added, and reaction was conducted between the Fc-binding protein and the immobilized gammaglobulin (at 30° C. for 1 hour).

(4-3) Upon completion of the reaction, it was rinsed with wash buffer and Anti-6His antibody (product of Bethyl Laboratories) diluted to 100 ng/mL was added at 100 μL/well.

(4-4) Reaction was conducted at 30° C. for 1 hour, and after rinsing with wash buffer, TMB Peroxidase Substrate (product of KPL) was added at 50 μL/well. Coloration was stopped by adding 1 M phosphoric acid at 50 μL/well, and the absorbance at 450 nm was measured with a microplate reader (product of Tecan).

(5) Approximately 2700 transformants were evaluated by the method of (4), and among these there were selected transformants expressing Fc-binding protein with increased stability compared to FcR35c. The selected transformants were cultured with 2YT liquid medium containing 50 μg/mL kanamycin, and an expression vector was prepared using a QIAprep Spin Miniprep kit (product of Qiagen Inc.).

(6) The sequence of the polynucleotide region encoding Fc-binding protein that had been inserted into the obtained expression vector was supplied to a cycle sequencing reaction using a BigDye Terminator Cycle Sequencing FS Read Reaction Kit (product of Thermo Fisher Scientific) based on the chain terminator method, and the nucleotide sequence was analyzed with a fully automatic DNA sequencer: ABI Prism 3700 DNA analyzer (product of Thermo Fisher Scientific). For the analysis, oligonucleotides comprising the sequences listed as SEQ ID NO: 2 (5'-TAATACGACTCAC-TATAGGG-3') and SEQ ID NO: 3 (5'-TATGCTAGTTAT-TGCTCAG-3') were used as the sequencing primers.

The transformants were evaluated by the method of (4) above and compared with FcR35c, giving the results shown in Table 2. The polypeptides with increased alkali stability compared to FcR35c were designated as FcR35d, FcR36i and FcR36a. The polypeptides with decreased alkali stability compared to FcR35c are listed as A, B, C and D in Table 2 (unconfirmed sequences).

TABLE 2

| Fc-binding protein | | Residual |
|---|---|---|
| Name | SEQ ID NO: | activity [%] |
| FcR35d | 7 | 45.1 |
| FcR36i | 9 | 43.5 |
| FcR36a | 11 | 43.0 |
| A | — | 40.0 |
| B | — | 39.0 |
| C | — | 35.5 |
| D | — | 17.6 |
| FcR35c | 5 | 42.2 |

The amino acid sequence of the Fc-binding protein containing FcR35d is listed as SEQ ID NO: 7, and the polynucleotide encoding that protein is listed as SEQ ID NO: 8. The amino acid sequence of the Fc-binding protein containing FcR36i is listed as SEQ ID NO: 9, and the polynucleotide encoding that protein is listed as SEQ ID NO: 10. The amino acid sequence of the Fc-binding protein containing FcR36a is listed as SEQ ID NO: 11, and the polynucleotide encoding that protein is listed as SEQ ID NO: 12. In SEQ ID NO: 7, 9 and 11, the region from methionine (Met) at position 1 to alanine (Ala) at position 26 is the MalE signal peptide, the region from lysine (Lys) at position 27 to methionine (Met) at position 32 is a linker sequence, the region from glycine (Gly) at position 33 to glutamine (Gln) at position 208 is the amino acid sequence of FcR35d (SEQ ID NO: 7), FcR36i (SEQ ID NO: 9) or FcR36a (SEQ ID NO: 11), the region of glycine (Gly) from position 209 to position 210 is a linker sequence, and the region of histidine (His) from position 211 to position 216 is the tag sequence.

As a result of analyzing the sequences of the polynucleotides encoding FcR35d, FcR36i and FcR36a by the method of (6) above, it was found that FcR35d (SEQ ID NO: 7) had produced the new amino acid substitutions of Ser81Arg, Asn196 Lys, Glu200Gly and Glu203Asp in FcR35c, while the amino acid residues at position 98, position 114, position 117 and position 208 had been restored to the amino acid residues of the wild-type (SEQ ID NO: 4). Also, FcR36i (SEQ ID NO: 9) had produced the new amino acid substitutions of Ser81Arg, Val192Ile, Asn196 Lys, Glu200Gly and Glu203Asp in FcR35c, while the amino acid residues at position 98, position 114, position 117 and position 208 had been restored to the amino acid residues of the wild-type (SEQ ID NO: 4), similar to FcR35d. FcR36a (SEQ ID NO: 11) had produced the new amino acid substitutions of Ser81Arg, Val192Ala, Asn196 Lys, Glu200Gly and Glu203Asp in FcR35c, while the amino acid residues at position 98, position 114, position 117 and position 208 had been restored to the amino acid residues of the wild-type (SEQ ID NO: 4), similar to FcR35d and FcR36i.

Example 3 Evaluation of Alkali Stability of Fc-Binding Proteins (1) Transformants expressing FcR35ε-containing Fc-binding protein (SEQ ID NO: 5), as well as the FcR35d-containing Fc-binding protein (SEQ ID NO: 7), FcR36i-containing Fc-binding protein (SEQ ID NO: 9) and FcR36α-containing Fc-binding protein (SEQ ID NO: 11), obtained in Example 2, were each inoculated onto 100 mL of 2YT liquid medium containing 50 μg/mL kanamycin, and aerobically shake cultured overnight at 37° C. as preculturing.

(2) This preculturing solution was inoculated at 10 mL into 1000 mL of 2YT liquid medium (16 g/L peptone, 10 g/L yeast extract and 5 g/L sodium chloride) containing 50 μg/mL added kanamycin, and aerobically shake cultured at 37° C.

(3) At 1.5 hours after the start of culturing, the culturing temperature was lowered to 20° C. and shake culturing was continued for 30 minutes. Next, IPTG was added to a final concentration of 0.01 mM, and aerobic shake culturing was continued overnight at 20° C.

(4) Upon completion of culturing, the cells were collected by centrifugal separation and suspended in buffer (20 mM Tris-HCl buffer containing 150 mM NaCl (pH 7.4)) and subjected to ultrasonic disruption. The supernatant was then collected by centrifugal separation.

(5) The collected supernatant was passed through a column packed with Ni Sepharose6 Fast Flow (GE Healthcare) and thoroughly washed with wash buffer (20 mM Tris-HCl buffer containing 150 mM NaCl (pH 7.4)), after which it was eluted with elution buffer (20 mM Tris-HCl buffer containing 150 mM NaCl and 500 mM imidazole (pH 7.4)) and the elution fraction was recovered.

(6) The elution fraction recovered in (5) was passed through a column packed with IgG Sepharose6 Fast Flow (GE Healthcare) and thoroughly washed with wash buffer (20 mM Tris-HCl buffer containing 150 mM NaCl (pH 7.4)), after which it was eluted with elution buffer (100 mM glycine buffer containing (pH 3.0)) and the elution fraction was recovered, and then a ¼-fold amount of 1 M Tris-HCl buffer (pH 8.0) was added for neutralization, to prepare each purified Fc-binding protein.

(7) After dilution with purified water to a 10 μg/mL concentration of each Fc-binding protein, 50 μL of the diluted solution and 50 μL of a 200 mM sodium hydroxide solution were mixed and the mixture was allowed to stand at 25° C. for 96 hours for alkali treatment. It was then neutralized by adding a 4-fold volume of 1 M Tris-HCl buffer (pH 7.0).

(8) The antibody-binding activity of the Fc-binding protein after the alkali treatment of (7) above and the antibody-binding activity of the Fc-binding protein without the alkali treatment of (7) were each measured by the ELISA method described in Example 2(4). The antibody-binding activity of the Fc-binding protein after the alkali treatment was then divided by the antibody-binding activity of the Fc-binding protein without alkali treatment to calculate the residual activity.

The results are shown in Table 3. The FcR35d-containing Fc-binding protein (SEQ ID NO: 7), FcR36i-containing Fc-binding protein (SEQ ID NO: 9) and FcR36α-containing Fc-binding protein (SEQ ID NO: 11) had high residual activity compared to the FcR35c-containing Fc-binding protein (SEQ ID NO: 5), and therefore FcR35d, FcR36i and FcR36a obtained in Example 2 were confirmed to have increased alkali stability (alkali resistance) compared to FcR35c.

TABLE 3

| Fc-binding protein | | Residual |
| --- | --- | --- |
| Name | SEQ ID NO: | activity [%] |
| FcR35d | 7 | 95.0 |
| FcR36i | 9 | 91.7 |
| FcR36a | 11 | 84.3 |
| FcR35c | 5 | 75.0 |

Example 4: Measurement of Binding Activity of Fc-Binding Protein for IgG

The transformants used were transformants expressing FcR35d-containing Fc-binding protein (SEQ ID NO: 7), FcR36i-containing Fc-binding protein (SEQ ID NO: 9), FcR36α-containing Fc-binding protein (SEQ ID NO: 11) or FcR35c-containing Fc-binding protein (SEQ ID NO: 5), and measurement was performed by the following method.

(1) Transformants expressing the FcR35d-containing Fc-binding protein (SEQ ID NO: 7) or FcR36i-containing Fc-binding protein (SEQ ID NO: 9) were each inoculated onto 2 mL of 2YT liquid medium containing 50 μg/mL kanamycin, and aerobically shake cultured overnight at 37° C. as preculturing.

(2) This preculturing solution was inoculated at 0.2 mL into 20 mL of 2YT liquid medium (16 g/L peptone, 10 g/L yeast extract and 5 g/L sodium chloride) containing 50 μg/mL added kanamycin, and aerobically shake cultured at 37° C.

(3) At 1.5 hours after the start of culturing, the culturing temperature was lowered to 20° C. and shake culturing was continued for 30 minutes. Next, IPTG ((isopropyl-β-thiogalactopyranoside) was added to a final concentration of 0.01 mM, and aerobic shake culturing was continued overnight at 20° C.

(4) Upon completion of culturing, the cells were collected by centrifugal separation and a BugBuster Protein extraction kit (product of Merck Millipore) was used to prepare a protein extract.

(5) The antibody-binding activity of the Fc-binding protein was measured by the ELISA method described in Example 2(4). The expression level of the Fc-binding protein was calculated based on the binding activity of the obtained Fc-binding protein for IgG.

The results are shown in Table 4. The expression levels of the Fc-binding proteins FcR35d and FcR36i per 1 L of culture solution were 443.5 mg and 495.6 mg, respectively.

TABLE 4

| Fc-binding protein | | Expression level [mg/L |
|---|---|---|
| Name | SEQ ID NO: | (culture solution)] |
| FcR35d | 7 | 443.5 |
| FcR36i | 9 | 495.6 |

(6) Transformants expressing FcR35d-containing Fc-binding protein (SEQ ID NO: 7), FcR36i-containing Fc-binding protein (SEQ ID NO: 9), FcR36α-containing Fc-binding protein (SEQ ID NO: 11) or FcR35ε-containing Fc-binding protein (SEQ ID NO: 5) were each inoculated onto 2 mL of 2YT liquid medium containing 50 μg/mL kanamycin, and aerobically shake cultured overnight at 37° C. as preculturing.

(7) Shake culture was carried out in the same manner as (2) above.

(8) Shake culture was carried out by the same method described in (3) above, except that the culturing time was 12 hours.

(9) A protein extract was prepared in the same manner as (4) above.

(10) The expression level was calculated in the same manner as (5) above.

The results are shown in Table 5. The expression levels of the Fc-binding proteins FcR35d, FcR36i, FcR36a and FcR35c per 1 L of culture solution were 226 mg, 248 mg, 307 mg and 211 mg, respectively.

TABLE 5

| Fc-binding protein | | Expression level [mg/L |
|---|---|---|
| Name | SEQ ID NO: | (culture solution)] |
| FcR35d | 7 | 226 |
| FcR36i | 9 | 248 |
| FcR36a | 11 | 307 |
| FcR35c | 5 | 211 |

Example 5: Evaluation of Binding Affinity Between Fc-Binding Proteins and IgG1

(1) Culturing and purification were carried out by the same methods as Example 3(1) and (6) to prepare Fc-binding proteins.

(2) The binding affinity between IgG1 and each Fc-binding protein recovered as the elution fraction in (1) was evaluated by the surface plasmon resonance method. For measurement of the binding affinity using the surface plasmon resonance method, a Biacore T100 (GE Healthcare) was used as the measuring apparatus, a Sensor Chip CM5 (GE Healthcare) was used as the sensor chip and Biacore T100 Evaluation Software (GE Healthcare) was used as the analysis software.

(3) An Amine Coupling Kit (GE Healthcare) was used for flow of a solution comprising IgG1 (product of Sigma-Aldrich) diluted with HBS-EP (GE Healthcare) on a sensor chip immobilizing the Fc-binding protein, to obtain a sensorgram. Curve fitting was carried out based on the sensorgram to calculate the binding affinity for IgG1.

The results of calculating the binding affinity for IgG1 are shown in Table 6. In Table 6, a lower $K_D$ value (dissociation constant) indicates higher affinity (binding affinity). The $K_D$ values for the FcR35d-containing Fc-binding protein (SEQ ID NO: 7), FcR36i-containing Fc-binding protein (SEQ ID NO: 9) and FcR36a-containing Fc-binding protein (SEQ ID NO: 11) were $3.9 \times 10^{-8}$ M, $4.3 \times 10^{-8}$ M and $9.5 \times 10^{-8}$ M, respectively, which were approximately equivalent to the $K_D$ value for the FcR35c-containing Fc-binding protein (SEQ ID NO: 5) ($4.0 \times 10^{-8}$ M).

TABLE 6

| Fc-binding protein | | Binding rate constant ka | Dissociation rate constant kd | Dissociation constant Kd |
|---|---|---|---|---|
| Name | SEQ ID NO: | [1/Ms] | [1/s] | [M] |
| FcR35d | 7 | $8.1 \times 10^5$ | $3.1 \times 10^{-2}$ | $3.9 \times 10^{-8}$ |
| FcR36i | 9 | $9.0 \times 10^5$ | $3.8 \times 10^{-2}$ | $4.3 \times 10^{-8}$ |
| FcR36a | 11 | $1.4 \times 10^6$ | $1.3 \times 10^{-1}$ | $9.5 \times 10^{-8}$ |
| FcR35c | 5 | $5.4 \times 10^5$ | $2.2 \times 10^{-2}$ | $4.0 \times 10^{-8}$ |

These results demonstrated that the FcR35d, FcR36i and FcR36a obtained in Example 2 have antibody-binding affinity similar to a known polypeptide that can bind to the antibody Fc region (FcR35c, Japanese Unexamined Patent Publication No. 2017-11887), while have increased alkali resistance.

Example 6: Construction of Cysteine Tag-Added FcR36i (1) PCR was conducted using a polynucleotide encoding the FcR36i constructed in Example 2 (SEQ ID NO: 10) as template. The primers used for PCR were oligonucleotides comprising the sequences listed as SEQ ID NO: 13 (5'-CATATGAAAATAAAAACAGGTGCACGCATCCTCG-CATTATCCGCATTAACGAC-3') and SEQ ID NO: 14 (5'-CCCAAGCTTATCCGCAGGTATCGTTGCGGCACCCT-TGGGTAACGGTAATGTCCACGG CCCCGCTG-3'). The PCR was conducted by preparing a reaction mixture with the composition shown in Table 7, and then heat treating the reaction mixture at 98° C. for 5 minutes, and repeating 30 cycles of a reaction where one cycle consisted of a first step at 98° C. for 10 seconds, a second step at 55° C. for 5 seconds and a third step at 72° C. for 1 minute.

TABLE 7

| Composition | Volume |
|---|---|
| Template DNA (concentration: 1 ng/μL) | 1 μL |
| 10 μM PCR primer (SEQ ID NO: 13) | 1.5 μL |
| 10 μM PCR primer (SEQ ID NO: 14) | 1.5 μL |
| 5 × PrimeSTAR buffer (Takara Bio, Inc.) | 10 μL |
| 2.5 mM dNTPs | 4 μL |
| 2.5 U/μL PrimeSTAR HS (Takara Bio, Inc.) | 0.5 μL |
| H$_2$O | up to 50 μL |

(2) The polynucleotide obtained in (1) was purified and digested with restriction enzymes NcoI and HindIII, and then ligated with expression vector pTrc-PelB constructed by the method described in WO2015/199154, which had been previously digested with restriction enzymes NcoI and HindIII, and the ligation product was used to transform *E. coli* W3110.

(3) The obtained transformants were cultured in LB medium containing 100 μg/mL carbenicillin, and then a QIAprep Spin Miniprep kit (product of Qiagen Inc.) was used to extract expression vector pTrc-FcR36i_Cys.

(4) The nucleotide sequence of pTrc-FcR36i_Cys was analyzed using oligonucleotides comprising the sequences listed as SEQ ID NO: 15 (5'-TGTGGTATGGCTGTGCAGG-3') and SEQ ID NO: 16 (5'-TCGGCATGGGGTCAGGTG-3').

The amino acid sequence of the polypeptide expressed by expression vector pTrc-FcR36i_Cys is listed as SEQ ID NO: 17, and the sequence of the polynucleotide encoding the polypeptide is listed as SEQ ID NO: 18.

In SEQ ID NO: 17, the sequence from methionine (Met) at position 1 to alanine (Ala) at position 22 is a modified PelB signal peptide (an oligopeptide comprising the amino acid residues from position 1 to position 22 of UniProt No. P0C1C1, with the stipulation that the oligopeptide includes one amino acid substitution), and the sequence from glycine (Gly) at position 24 to glutamine (Gln) at position 199 is the amino acid sequence of Fc-binding protein FcR36i (the region from position 33 to position 208 of SEQ ID NO: 9), while the sequence from glycine (Gly) at position 200 to glycine (Gly) at position 207 is the cysteine tag sequence.

Example 7: Preparation of FcR36i_Cys (1) Transformants expressing the FcR36i_Cys constructed in Example 6 were inoculated into 400 mL of 2YT liquid medium (16 g/L peptone, 10 g/L yeast extract and 5 g/L sodium chloride) containing 100 μg/mL carbenicillin in a 2 L baffle flask, and aerobically shake cultured overnight at 37° C., as preculturing.

(2) After inoculating 180 mL of the culture solution of (1) into 1.8 L of liquid medium containing 10 g/L glucose, 20 g/L yeast extract, 3 g/L trisodium phosphate dodecahydrate, 9 g/L disodium hydrogen phosphate dodecahydrate, 1 g/L ammonium chloride and 100 mg/L carbenicillin, a 3 L fermenter (product of Biott) was used for main culturing. The conditions were set to a temperature of 30° C., a pH of 6.9 to 7.1, an aeration rate of 1 VVM and a dissolved oxygen concentration at 30% saturated concentration, and main culturing was commenced. For pH regulation, 50% phosphoric acid was used as the acid and 14% ammonia water was used as the alkali, the dissolved oxygen was controlled by varying the stirring speed, and the stirring rotational speed was set with a lower limit of 500 rpm and an upper limit of 1000 rpm. When the glucose concentration was no longer measurable after the start of culturing, feeding culture medium (248.9 g/L glucose, 83.3 g/L yeast extract, 7.2 g/L magnesium sulfate heptahydrate) was added while controlling the dissolved oxygen (DO).

(3) When the absorbance at 600 nm (OD600 nm) reached about 150 as a measure of the cell mass, the culturing temperature was lowered to 25° C., and upon confirming that the preset temperature had been reached, IPTG (isopropyl β-D-1-thiogalactopyranoside) was added to a final concentration of 0.5 mM and culturing was continued at 25° C.

(4) Culturing was terminated at about 48 hours after the start of culturing, and the cells were recovered by centrifugation of the culture solution at 8000 rpm for 20 minutes at 4° C.

(5) The collected cells were suspended in 20 mM phosphate buffer (pH 7.0) to 5 mL/1 g (cells), and an ultrasonic generator (INSONATOR 201M, trade name of Kubota Corp.) was used to disrupt the cells at 4° C. for about 10 minutes, with an output of about 150 W. The cell disruptate was centrifuged twice at 4° C. for 20 minutes, 8000 rpm, and the supernatant was collected.

(6) The supernatant obtained in (5) was applied to a VL32×250 column (Merck Millipore) packed with 140 mL of TOYOPEARL CM-650 M (Tosoh Corp.) previously equilibrated with 20 mM phosphate buffer (pH 7.0), at a flow rate of 10 mL/min. After rinsing with the buffer used for equilibration, it was eluted with 20 mM phosphate buffer (pH 7.0) containing 0.8 M sodium chloride.

The purification described above yielded FcR36i_Cys.

Example 8: Preparation of FcR36i-Immobilized Gel and Antibody Isolation by Linear Gradient Elution (1) After activating the hydroxyl groups on the surface of a hydrophilic vinyl polymer for separation (Tosoh Corp.) using iodoacetyl groups, it was reacted with the FcR36i_Cys prepared in Example 7 to obtain an FcR36i-immobilized gel.

(2) A 1.0 mL portion of the FcR36i-immobilized gel prepared in (1) was packed into a Tricorn column (product of GE Healthcare, inner diameter: 5 mm).

(3) The column packed with the FcR36i-immobilized gel was connected to an AKTA Avant (GE Healthcare) and equilibrated with 20 mM acetate buffer at pH 4.8 (buffer A).

(4) A 0.5 mL portion of 10 mg/mL of monoclonal antibody (Rituxan, product of Zenyaku Kogyo) was applied with 20 mM acetate buffer at pH 4.8 (buffer A), at a flow rate of 0.2 mL/min.

(5) After rinsing for 66 minutes with equilibrating buffer while maintaining a flow rate of 0.2 mL/min, the monoclonal antibody adsorbed with a linear gradient produced with 10 mM glycine hydrochloride buffer at pH 3.0 (buffer B) (a linear gradient for 100% of the 10 mM glycine hydrochloride buffer at pH 3.0 (buffer B) in 75 minutes) was eluted.

The result (elution pattern chromatogram) is shown in FIG. 2. The monoclonal antibody interacting with FcR36i separated not into a single peak as in gel filtration chromatography, but into two peaks. Specifically, the antibody exhibiting weak binding with FcR36i had a rapid elution time while the antibody exhibiting strong binding had a slow elution time, and thus separated into two peaks.

Example 9: ADCC (Antibody-Dependent Cell-Mediated Cytotoxicity) Activity Measurement of Antibody Separated by Linear Gradient Elution Using FcR36i-Immobilized Gel (1) A monoclonal antibody was isolated under the elution conditions described in Example 8 and fractionated into fraction A (FrA) and fraction B (FrB) in the elution pattern chromatogram shown in FIG. 2.

(2) The concentrations of the antibodies included in FrA and FrB and of the monoclonal antibodies before isolation were measured at an absorbance of 280 nm.

(3) The ADCC activities of the antibodies included in FrA and FrB and the monoclonal antibodies before isolation were measured by the following method.

(3-1) Using ADCC Assay Buffer prepared by mixing 1.4 mL of Low IgG Serum and 33.6 mL of RPMI 1640 medium, a 9-step dilution series from 1 ng/mL to 1/3 dilution was prepared from the antibodies included in FrA and FrB and the monoclonal antibodies before isolation.

(3-2) Raji cells were prepared to approximately $5 \times 10^5$ cells/mL with ADCC Assay Buffer, and added to a 96-well plate (3917: Corning, Inc.) at 25 μL/well.

(3-3) The monoclonal antibodies of FrA, FrB and before isolation, prepared in (3-1), and a blank (ADCC Assay Buffer alone), were added to the Raji cell-added wells at 25 μL/well.

(3-4) Effector cells (Promega) were prepared to approximately $3.0\times10^5$ cells/mL with ADCC Assay Buffer, and added to the wells containing the Raji cells and antibodies at 25 µL/well. The mixture was then allowed to stand for 6 hours in a $CO_2$ incubator (5% $CO_2$, 37° C.).

(3-5) After allowing the 96-well plate to stand for 5 minutes to 30 minutes at room temperature, Luciferase Assay Reagent (Promega) was added at 75 µL/well. Following reaction for 30 minutes at room temperature, the luminescence was measured with a GloMax Multi Detection System (Promega).

FIG. 3 shows the results of comparing the luminous intensities of the antibodies in FrA and FrB fractionated under the elution conditions described in Example 8, and the monoclonal antibodies before isolation. The results in FIG. 3 are shown as the value of the measured luminous intensity minus the luminous intensity of the blank, with a higher luminous intensity representing higher ADCC activity.

The antibody in FrA with a rapid elution time, which was separated by the FcR36i-immobilized gel, had about the same luminous intensity as the monoclonal antibody before separation, and therefore their ADCC activities may be considered to be approximately equal.

The antibody in FrB with a slow elution time had ADCC activity increased by about 1.4 times compared to the monoclonal antibody before separation, and by about 1.5 times compared to the antibody in FrA as well. In other words, the antibody in FrB had higher ADCC activity than the monoclonal antibody before separation and the antibody in FrA.

Example 10: Sugar Chain Structure Analysis of Antibodies Separated by Linear Gradient Elution Using FcR36i-Immobilized Gel (1) After denaturing the respective antibodies in FrA and FrB that had been fractionated in Example 9(1), by heat treatment at 100° C. for 10 minutes, they were treated with glycoamidase A/pepsin and pronase in that order, and subjected to a purification procedure by gel filtration to obtain the sugar chain fraction.

(2) The sugar chains obtained in (1) were concentrated and dried with an evaporator, and then reacted with 2-aminopyridine and dimethylamineborane in that order in an acetic acid solvent to obtain fluorescent-labeled sugar chains, which were purified by gel filtration.

(3) The fluorescent-labeled sugar chains obtained in (2) were separated into a neutral sugar chain fraction and a monosialylated sugar chain fraction, using an anion exchange column (TSKgel DEAE-SPW, φ7.5 mm×7.5 cm, product of Tosoh Corp.).

(4) The neutral sugar chain fraction and monosialylated sugar chain fraction obtained in (3) were isolated into individual sugar chains using an ODS column. After obtaining molecular weight information for the isolated sugar chains by MALDI-TOF-MS analysis, the sugar chain structures were assigned, taking into account the retention time of the ODS column chromatograph.

Figure 4:
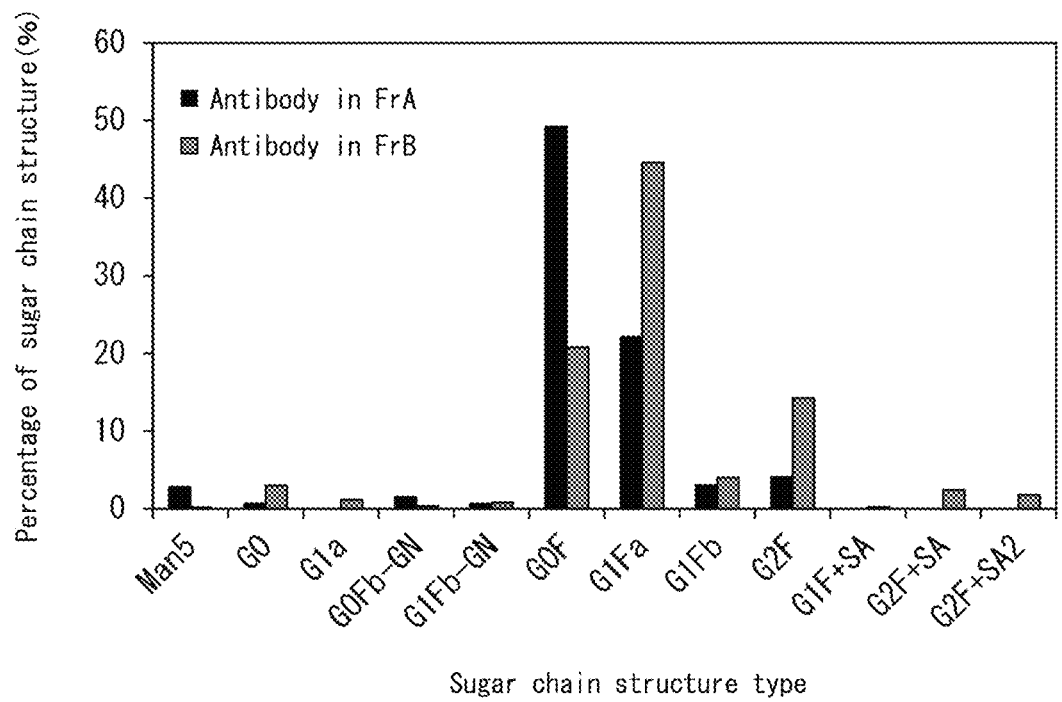
FIG. 4 shows the results of analyzing the sugar chain structure of a monoclonal antibody (Rituxan) separated by linear gradient elution using FcR36i-immobilized gel.

The results of the assigned sugar chain structures are shown in FIG. 4 and Table 8, and schematic diagrams of the sugar chain structures are shown in Table 9. The proportion of antibodies with sugar chain structures containing galactose at the end (G1Fa and G2F) was higher and the proportion of antibodies with sugar chain structures without galactose at the end (G0F) was lower, with the antibody in FrB compared to the antibody in FrA. This indicates that an antibody having a sugar chain structure with galactose at the end binds strongly to FcR36i, and elutes with a slow elution time (i.e. it elutes at a low pH) when separated with Fc36i-immobilized gel, while an antibody having a sugar chain structure without galactose at the end has weak binding strength with FcR36i, and elutes rapidly (i.e. it elutes at a high pH) during separation with Fc36i-immobilized gel.

TABLE 8

| Name of sugar chain structure | Percentage of sugar chain structure (%) | |
| --- | --- | --- |
| | FrA | FrB |
| Man5 | 2.8 | 0.2 |
| G0 | 0.7 | 3.0 |
| G1a | — | 1.2 |
| G0F | 49.2 | 20.8 |
| G1Fa | 22.1 | 44.6 |
| G1Fb | 3.0 | 4.0 |
| G2F | 4.1 | 14.3 |
| G1F + SA | — | 0.2 |
| G2F + SA | — | 2.4 |
| G2F + SA2 | — | 1.8 |
| Unknown structure | 15.9 | 6.3 |
| Other | 2.2 | 1.2 |

TABLE 9

| Name of sugar chain structure | Name of sugar chain structure |
| --- | --- |
| Man5 | Manα1-6\<br>Manα1-3 ⟩Manα1-6\<br>Manα1-3 ⟩Manβ1-4GlcNAcβ1-4GlcNAc-PA |
| G0 | GlcNAcβ1-2Manα1-6\<br>GlcNAcβ1-2Manα1-3 ⟩Manβ1-4GlcNAcβ1-4GlcNAc-PA |
| G1a | Galβ1-4GlcNAcβ1-2Manα1-6\<br>GlcNAcβ1-2Manα1-3 ⟩Manβ1-4GlcNAcβ1-4GlcNAc-PA |
| G0F | GlcNAcβ1-2Manα1-6\<br>GlcNAcβ1-2Manα1-3 ⟩Manβ1-4GlcNAcβ1-4GlcNAc-PA (Fucα1-6) |

TABLE 9-continued

| Name of sugar chain structure | Name of sugar chain structure |
|---|---|
| G1Fa | Galβ1-4GlcNAcβ1-2Manα1-6<br>　　　　　　　　　　　　＼Fucα1-6<br>　　　　　　　　　　　　　＼<br>　　　　　　　　　　　　　Manβ1-4GlcNAcβ1-4GlcNAc-PA<br>GlcNAcβ1-2Manα1-3／ |
| G1Fb | GlcNAcβ1-2Manα1-6<br>　　　　　　　　　　　＼Fucα1-6<br>　　　　　　　　　　　　＼<br>　　　　　　　　　　　　Manβ1-4GlcNAcβ1-4GlcNAc-PA<br>Galβ1-4GlcNAcβ1-2Manα1-3／ |
| G2F | Galβ1-4GlcNAcβ1-2Manα1-6<br>　　　　　　　　　　　　＼Fucα1-6<br>　　　　　　　　　　　　　＼<br>　　　　　　　　　　　　　Manβ1-4GlcNAcβ1-4GlcNAc-PA<br>Galβ1-4GlcNAcβ1-2Manα1-3／ |
| G1F + SA | NeuAcα2-3Gal- { GlcNAcβ1-2Manα1-6<br>　　　　　　　　　　　　　　＼Fucα1-6<br>　　　　　　　　　　　　　　　＼<br>　　　　　　　　　　　　　　　Manβ1-4GlcNAcβ1-4GlcNAc-PA<br>　　　　　　　　GlcNAcβ1-2Manα1-3／ |
| G2F + SA | NeuAc- { Galβ1-4GlcNAcβ1-2Manα1-6<br>　　　　　　　　　　　　　　　＼Fucα1-6<br>　　　　　　　　　　　　　　　　＼<br>　　　　　　　　　　　　　　　　Manβ1-4GlcNAcβ1-4GlcNAc-PA<br>　　　　　Galβ1-4GlcNAcβ1-2Manα1-3／ |
| G2F + SA2 | NeuAcα2-3Galβ1-4GlcNAcβ1-2Manα1-6<br>　　　　　　　　　　　　　　　　　　＼Fucα1-6<br>　　　　　　　　　　　　　　　　　　　＼<br>　　　　　　　　　　　　　　　　　　　Manβ1-4GlcNAcβ1-4GlcNAc-PA<br>NeuAcα2-3Galβ1-4GlcNAcβ1-2Manα1-3／ |

NeuAc: N-acetylneuraminic acid,
Gal: galactose,
GlcNAc: N-acetylglucosamine,
Man: mannose,
Fuc: fucose,
PA: 2-aminopyridine (fluorescent labeling)

Example 11: Preparation of FcR36i-Immobilized Gel and Antibody Isolation by Step Gradient Elution (1) An FcR36i-immobilized gel was obtained by the same method as Example 8(1).

(2) The FcR36i-immobilized gel was packed into a column by the same method as Example 8(2).

(3) The column packed with the FcR36i-immobilized gel was connected to an AKTA Avant (GE Healthcare) and equilibrated with 20 mM acetate buffer (pH 5.2).

(4) A 1.5 mL portion of 10 mg/mL of monoclonal antibody (Rituxan, product of Zenyaku Kogyo) was applied with 20 mM acetate buffer (pH 5.2), at a flow rate of 0.2 mL/min.

(5) After conveying 20 mM acetate buffer (pH 5.2) for 120 minutes while maintaining a flow rate 0.2 mL/min, 20 mM acetate buffer (pH 4.8) was conveyed for 100 minutes at a flow rate of 0.2 mL/min to elute a monoclonal antibody.

(6) Next, 10 mM glycine hydrochloride buffer (pH 3.0) was conveyed for 50 minutes while maintaining a flow rate of 0.2 mL/min, to elute an adsorbed monoclonal antibody.

Figure 5:
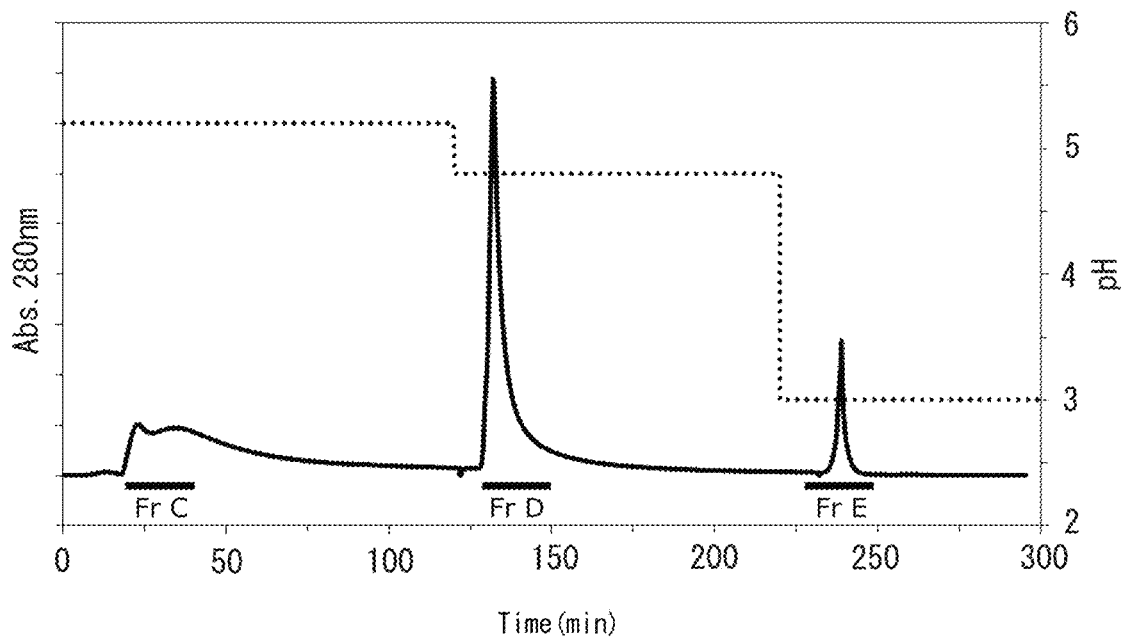
FIG. 5 is a chromatogram obtained upon separating a monoclonal antibody (Rituxan) with FcR36i-immobilized gel. Rituxan was eluted using 20 mM acetate buffer (pH 5.2), 20 mM acetate buffer (pH 4.8) and 10 mM glycine hydrochloride buffer (pH 3.0), by step gradient elution.

The result (elution pattern chromatogram) is shown in FIG. 5. By conveying buffers of different pH into the column, different antibodies were eluted with the buffers, with monoclonal antibodies being separated into three peaks. Since the monoclonal antibodies interact with FcR36i, it is understood that the antibody that eluted rapidly at a high pH is the antibody exhibiting weak affinity for FcR36i while the antibody that eluted slowly at low pH is the antibody exhibiting high affinity for FcR36i.

Example 12: Sugar Chain Analysis of Antibodies Separated by FcR36i-Immobilized Gel (1) Monoclonal antibodies were isolated under the elution conditions described in Example 11 and fractionated into fraction C (FrC), fraction D (FrD) and fraction E (FrE) in the elution pattern chromatogram shown in FIG. 5.

(2) The sugar chain structures were assigned by the same method as Example 10, except for using the respective antibodies in FrC, FrD and FrE fractionated as described above.

Figure 6:
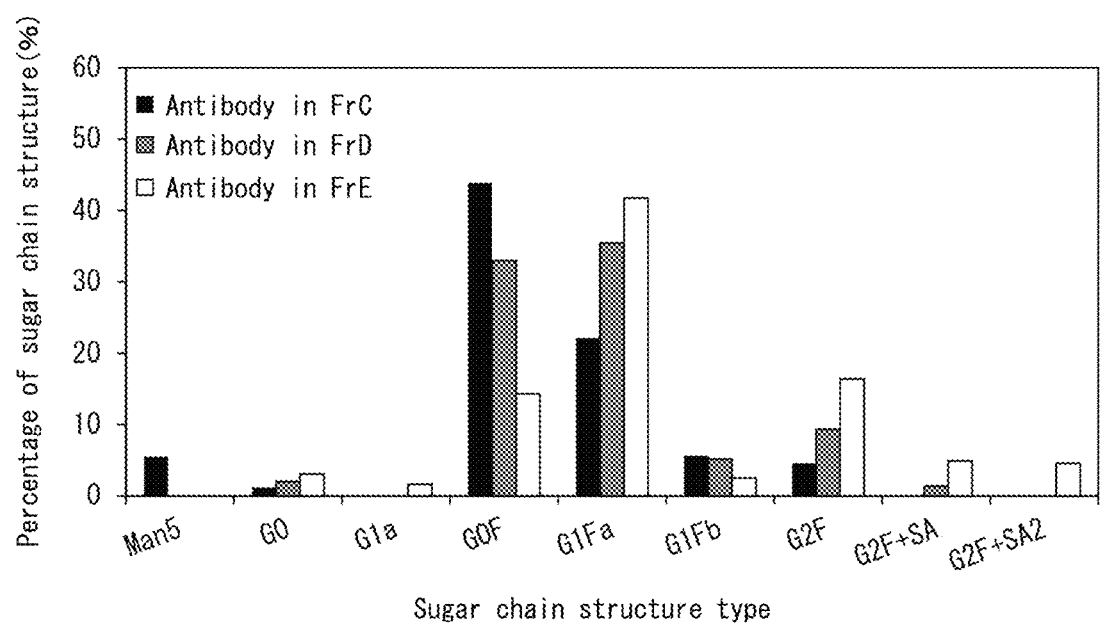
FIG. 6 shows the results of analyzing the sugar chain structure of a monoclonal antibody (Rituxan) separated by step gradient elution using FcR36i-immobilized gel.

The results of the assigned sugar chain structures are shown in FIG. 6 and Table 10, and schematic diagrams of the sugar chain structures are shown in Table 9.

Upon comparing the sugar chain structures of each of the antibodies in FrC (eluted with 20 mM acetate buffer (pH 5.2)), FrD (eluted with 20 mM acetate buffer (pH 4.8)) and FrE (eluted with 10 mM glycine hydrochloride buffer (pH 3.0)), the proportion of antibodies with a galactose-free sugar chain structure (G0F) at the ends was higher with the antibodies contained in the fraction eluted at high pH, while the proportion of antibodies with galactose-containing sugar chain structures (G1Fa and G2F) at the ends was higher with the antibodies contained in the fraction eluted at low pH. This indicates that an antibody having a sugar chain structure with galactose at the end binds strongly to FcR36i, and elutes at a low pH when separated with Fc36i-immobilized gel, while an antibody having a sugar chain structure without galactose at the end has weak binding strength with FcR36i, and elutes at a high pH during separation with Fc36i-immobilized gel.

TABLE 10

| Name of sugar chain structure | Percentage of sugar chain structure (%) | | |
|---|---|---|---|
| | FrC | FrD | FrE |
| Man5 | 5.5 | — | — |
| G0 | 1.2 | 2.0 | 3.1 |
| G1a | — | — | 1.6 |
| G0F | 43.9 | 33.0 | 14.3 |
| G1Fa | 22.2 | 35.5 | 41.8 |
| G1Fb | 5.7 | 5.2 | 2.5 |
| G2F | 4.6 | 9.4 | 16.4 |
| G2F + SA | — | 1.4 | 4.9 |
| G2F + SA2 | — | — | 4.6 |
| Unknown structure | 13.0 | 13.3 | 10.7 |
| Other | 3.6 | — | — |

Example 13: Antibody Isolation by Step Gradient Elution Using FcR36i-Immobilized Gel (2)

(1) An FcR36i-immobilized gel was obtained by the same method as Example 8(1).
(2) The FcR36i-immobilized gel was packed into a column by the same method as Example 8(2), except that the amount of gel was 0.2 mL
(3) The column packed with the FcR36i-immobilized gel was connected to an AKTA Avant (GE Healthcare) and equilibrated with 20 mM acetate buffer (pH 5.2).
(4) A 0.3 mL portion of 10 mg/mL of monoclonal antibody (Avastin, product of Roche) was applied with 20 mM acetate buffer (pH 5.2), at a flow rate of 0.04 mL/min.
(5) After conveying 20 mM acetate buffer (pH 5.2) for 180 minutes while maintaining a flow rate 0.04 mL/min, 20 mM acetate buffer (pH 4.8) was conveyed for 150 minutes at a flow rate of 0.04 mL/min to elute a monoclonal antibody.
(6) Next, 10 mM glycine hydrochloride buffer (pH 3.0) was conveyed for 100 minutes while maintaining a flow rate of 0.04 mL/min, to elute the adsorbed monoclonal antibody.

Figure 7:
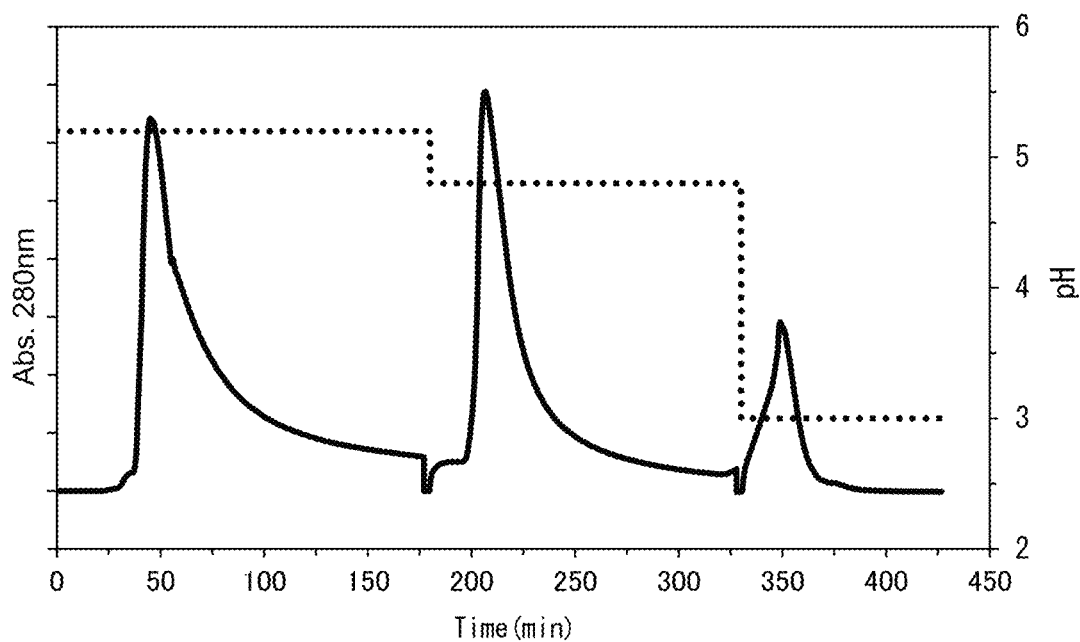
FIG. 7 is a chromatogram obtained upon separating a monoclonal antibody (Avastin) with FcR36i-immobilized gel. Avastin was eluted using 20 mM acetate buffer (pH 5.2), 20 mM acetate buffer (pH 4.8) and 10 mM glycine hydrochloride buffer (pH 3.0), by step gradient elution.

The resulting (elution pattern chromatogram) is shown in FIG. 7. The monoclonal antibodies separated into three peaks, but since they were antibodies of a different type than Example 11, a different elution pattern was obtained.

Reference Example 1: Construction of Amino Acid-Substituted FcR9

The following amino acid substitution was carried out in Fc-binding protein FcR9 (SEQ ID NO: 20) prepared by the method described in Japanese Unexamined Patent Publication No. 2016-169197 (PTL 3), in order to confirm the efficacy of substituting the amino acid residue at position 192 (corresponding to position 176 in SEQ ID NO: 1) with other amino acids. Specifically, amino acid substitution was carried out with plasmid pET-FcR9 containing a polynucleotide encoding FcR9 (SEQ ID NO: 21) (Japanese Unexamined Patent Publication No. 2016-169197) using PCR, to prepare Fc-binding protein having valine at position 192 of FcR9 (SEQ ID NO: 20) substituted with other amino acids. Incidentally, FcR9 (SEQ ID NO: 20) is an Fc-binding protein having the amino acid substitutions of glutamic acid for valine at position 43 (corresponding to position 27 in SEQ ID NO: 1), isoleucine for phenylalanine at position 45 (corresponding to position 29 in SEQ ID NO: 1), asparagine for tyrosine at position 51 (corresponding to position 35 in SEQ ID NO: 1), arginine for glutamine at 64th (corresponding to position 48 in SEQ ID NO: 1), leucine for phenylalanine at position 91 (corresponding to position 75 in SEQ ID NO: 1), serine for asparagine at position 108 (corresponding to position 92 in SEQ ID NO: 1), glutamic acid for valine at position 133 (corresponding to position 117 in SEQ ID NO: 1), glycine for glutamic acid at position 137 (corresponding to position 121 in SEQ ID NO: 1) and serine for phenylalanine at position 187 (corresponding to position 171 in SEQ ID NO: 1), in the Fc-binding protein comprising the human FcγRIII extracellular domain listed as SEQ ID NO: 4.

(1) A reaction mixture was prepared comprising the composition listed in Table 11, using plasmid pET-FcR9 (Japanese Unexamined Patent Publication No. 2016-169197) containing a polynucleotide (SEQ ID NO: 21) encoding FcR9 (SEQ ID NO: 20) constructed by the method described in Japanese Unexamined Patent Publication No. 2016-169197, as template DNA, an oligonucleotide comprising the sequence listed as SEQ ID NO: 2 (5'-TAATACGACTCACTATAGGG-3') as the forward primer and an oligonucleotide comprising the sequence listed as SEQ ID NO: 22 (5'-CATTTTTGCTGCCMNNCAGCC-CACGGCAGG-3') as the reverse primer, and then PCR was conducted, by heat treatment of the reaction mixture at 95° C. for 2 minutes, 30 cycles of reaction where 1 cycle consisted of a first step at 95° C. for 30 seconds, a second step at 50° C. for 30 seconds and a third step at 72° C. for 90 seconds, and finally heat treatment at 72° C. for 7 minutes. The obtained PCR product was designated as V192p1.

TABLE 11

| Composition | Volume |
|---|---|
| Template DNA | 2 μL |
| 10 μM Forward primer | 1 μL |
| 10 μM Reverse primer | 1 μL |
| 5 × PrimeSTAR buffer (Takara Bio, Inc.) | 4 μL |
| 2.5 mM dNTPs | 2 μL |
| 2.5 U/μL PrimeSTAR HS (Takara Bio, Inc.) | 0.5 μL |
| $H_2O$ | up to 20 μL |

(2) PCR was conducted by the same method as (1) above, except for using an oligonucleotide comprising the sequence listed as SEQ ID NO: 23 (5'-CCTGCCGTGGGCTGNNKGGCAGCAAAAATG-3') as the forward primer and an oligonucleotide comprising the sequence listed as SEQ ID NO: 3 (5'-TATGCTAGTTAT-TGCTCAG-3') as the reverse primer, and the obtained PCR product was designated as V192p2.

(3) A mixture of the V192p1 obtained in (1) and the V192p2 obtained in (2) as PCR products, was used to prepare a reaction mixture having the composition shown in Table 12, and the reaction mixture was then heat treated at 98° C. for 5 minutes, after which PCR was conducted by 5 cycles of reaction, where one cycle consisted of a first step at 98° C. for 10 seconds, a second step at 55° C. for 5 seconds and a third step at 72° C. for 1 minute, to obtain a PCR product V192p in which V192p1 and V192p2 were linked.

TABLE 12

| Composition | Volume |
|---|---|
| PCR product | 1 μL each |
| 2.5 U/μL PrimeSTAR HS (Takara Bio, Inc.) | 0.5 μL |

TABLE 12-continued

| Composition | Volume |
|---|---|
| 5 × PrimeSTAR buffer (Takara Bio, Inc.) | 4 µL |
| 2.5 mM dNTPs | 2 µL |
| H₂O | up to 20 µL |

(4) After preparing a reaction mixture with the composition shown in Table 13 using the V192p obtained in (3) as the PCR product, an oligonucleotide comprising the sequence listed as SEQ ID NO: 2 as the forward primer and an oligonucleotide comprising the sequence listed as SEQ ID NO: 3 as the reverse primer, the reaction mixture was heat treated at 98° C. for 5 minutes, and then PCR was conducted by 30 cycles of reaction, where one cycle consisted of a first step at 98° C. for 10 seconds, a second step at 55° C. for 5 seconds and a third step at 72° C. for 1 minute, to obtain a polynucleotide encoding Fc-binding protein having valine at position 192 of FcR9 (SEQ ID NO: 20) substituted with an arbitrary amino acid. The obtained polynucleotide was designated as V192p3.

TABLE 13

| Composition | Volume |
|---|---|
| PCR product | 2 µL |
| 10 µM Forward primer | 2 µL |
| 10 µM Reverse primer | 2 µL |
| 5 × PrimeSTAR buffer (Takara Bio, Inc.) | 10 µL |
| 2.5 mM dNTPs | 4 µL |
| 2.5 U/µL PrimeSTAR HS (Takara Bio, Inc.) | 1 µL |
| H₂O | up to 50 uL |

(5) The V192p3 obtained in (4) was purified and then digested with restriction enzymes NcoI and HindIII and ligated with the expression vector pETMalE previously digested with restriction enzymes NcoI and HindIII (Japanese Unexamined Patent Publication No. 2011-206046), and the ligation product was used for transformation of *E. coli* BL21 (DE3).

(6) The obtained transformants were cultured on LB medium containing 50 µg/mL added kanamycin. Plasmids were extracted from the collected cells (transformants).

(7) The polynucleotide encoding Fc-binding protein and its surrounding regions in the obtained plasmids was supplied for cycle sequencing reaction using a BigDye Terminator v3.1 Cycle Sequencing Kit (product of Life Technologies Corp.) based on the chain terminator method, and the nucleotide sequence was analyzed with a fully automatic DNA sequencer, Applied Biosystems 3130 Genetic Analyzer (product of Life Technologies Corp.). For the analysis, an oligonucleotide comprising the sequence listed as SEQ ID NO: 2 or SEQ ID NO: 3 was used as the sequencing primer.

As a result of the sequence analysis, transformants were obtained expressing Fc-binding proteins in which valine at position 192 of Fc-binding protein FcR9 (SEQ ID NO: 20) was substituted with alanine, arginine, asparagine, aspartic acid, cysteine, glutamine, glutamic acid, glycine, histidine, isoleucine, leucine, lysine, methionine, phenylalanine, proline, serine, threonine, tryptophan or tyrosine.

Reference Example 2: Measurement of Binding Activity of Fc-Binding Protein for IgG (1) Among the transformants obtained in Reference Example 1, the transformants expressing Fc-binding proteins in which the amino acid residue at position 192 of FcR9 (SEQ ID NO: 20) (position 176 in SEQ ID NO: 1) was substituted with isoleucine (hereunder indicated as Val192Ile), alanine (hereunder indicated as Val192Ala) or tyrosine (hereunder indicated as Val192Tyr) were each inoculated onto 2 mL of 2YT liquid medium containing 50 µg/mL kanamycin, and precultured overnight at 37° C. by aerobic shake culture.

(2) This preculturing solution was inoculated at 0.2 mL into 20 mL of 2YT liquid medium (16 g/L peptone, 10 g/L yeast extract and 5 g/L sodium chloride) containing 50 µg/mL added kanamycin, and aerobically shake cultured at 37° C.

(3) At 1.5 hours after the start of culturing, the culturing temperature was lowered to 20° C. and shake culturing was continued for 30 minutes. Next, IPTG ((isopropyl-β-thiogalactopyranoside) was added to a final concentration of 0.01 mM, and aerobic shake culturing was continued overnight at 20° C.

(4) Upon completion of culturing, the cells were collected by centrifugal separation and a BugBuster Protein extraction kit (product of Takara Bio, Inc.) was used to prepare a protein extract.

(5) The antibody-binding activity of the Fc-binding protein was measured by the ELISA method described below.

(5-1) A gammaglobulin preparation (by Kaketsuken) as the human antibody, was added to and immobilized in the wells of a 96-well microplate at 1 µg/well (at 4° C. overnight), and then blocking was performed by addition of 20 mM Tris-HCl buffering solution (pH 7.4) containing 2% (w/v) SKIM MILK (product of BD Co.) and 150 mM sodium chloride to the wells.

(5-2) After rinsing with wash buffer (20 mM Tris-HCl buffer (pH 7.4) containing 0.05% (w/v) Tween 20 and 150 mM NaCl), a solution containing Fc-binding protein for evaluation of the antibody-binding activity was added, and reaction was conducted between the Fc-binding protein and the immobilized gammaglobulin (at 30° C. for 1 hour).

(5-3) Upon completion of the reaction, it was rinsed with wash buffer, and Anti-6His antibody (product of Bethyl Laboratories) diluted to 100 ng/mL was added at 100 µL/well.

(5-4) Reaction was conducted at 30° C. for 1 hour, and after rinsing with wash buffer, TMB Peroxidase Substrate (product of KPL) was added at 50 µL/well. Coloration was stopped by adding 1 M phosphoric acid at 50 µL/well, and the absorbance at 450 nm was measured with a microplate reader (product of Tecan).

(6) The expression level of the Fc-binding protein obtained by the method of (5) above was calculated based on the binding activity of the obtained Fc-binding protein for IgG.

The results are shown in Table 14. The Fc-binding protein expression levels per 1 L of culture solution were 130.6 mg, 21.7 mg and 14.6 mg by the respective transformants expressing FcR9_I (SEQ ID NO: 24) as the Fc-binding protein containing the amino acid substitution Val192Ile, FcR9_A (SEQ ID NO: 26) as the Fc-binding protein containing the amino acid substitution Val192Ala, and FcR9_Y (SEQ ID NO: 28) as the Fc-binding protein containing the amino acid substitution Val192Tyr.

The amino acid sequence of FcR9_I as the Fc-binding protein examined for this Reference Example is listed as SEQ ID NO: 24, and the sequence of the polynucleotide encoding FcR9_I is listed as SEQ ID NO: 25. In SEQ ID NO: 24, the region from methionine (Met) at position 1 to alanine (Ala) at position 26 is the MalE signal peptide, the region from lysine (Lys) at position 27 to methionine (Met) at position 32 is a linker sequence, the region from glycine (Gly) at position 33 to glutamine (Gln) at position 208 is a polypeptide with the amino acid substitution Val192Ile in the amino acid sequence from glycine (Gly) at position 33 to glutamine (Gln) at position 208 of FcR9 (SEQ ID NO: 20), the region of glycine (Gly) from position 209 to position 210 is a linker sequence, and the region of histidine (His) from position 211 to position 216 is the tag sequence. The isoleucine of Val192Ile is also present at position 192 in SEQ ID NO: 24.

The amino acid sequence of FcR9_A as the Fc-binding protein examined for this Reference Example is listed as SEQ ID NO: 26, and the sequence of the polynucleotide encoding FcR9_A is listed as SEQ ID NO: 27. Incidentally, SEQ ID NO: 26 is the same sequence as SEQ ID NO: 24, except that the region from glycine (Gly) at position 33 to glutamine (Gln) at position 208 is a polypeptide with the amino acid substitution Val192Ala in the amino acid sequence from glycine (Gly) at position 33 to glutamine (Gln) at position 208 of FcR9 (SEQ ID NO: 20). The alanine of Val192Ala is also present at position 192 in SEQ ID NO: 26.

The amino acid sequence of FcR9_Y as the Fc-binding protein examined for this Reference Example is listed as SEQ ID NO: 28, and the sequence of the polynucleotide encoding FcR9_Y is listed as SEQ ID NO: 29. Incidentally, SEQ ID NO: 28 is the same sequence as SEQ ID NO: 24, except that the region from glycine (Gly) at position 33 to glutamine (Gln) at position 208 is a polypeptide with the amino acid substitution Val192Tyr in the amino acid sequence from glycine (Gly) at position 33 to glutamine (Gln) at position 208 of FcR9 (SEQ ID NO: 20). The tyrosine of Val192Tyr is also present at position 192 in SEQ ID NO: 28.

TABLE 14

| Reference Example | Fc-binding protein Name | Amino acid substitution | Expression level [mg/L (culture solution)] |
| --- | --- | --- | --- |
| Reference Example 2 | FcR9_I | Val192Ile | 130.6 |
| | FcR9_A | Val192Ala | 21.69 |
| | FcR9_Y | Val192Tyr | 14.60 |
| Reference Example 3 | FcR9 | — | 1.387 |
| Reference Example 4 | FcR9_F | Val192Phe | 0.263 |
| | FcR9_R | Val192Arg | 0.254 |
| | FcR9_L | Val192 Leu | 0.192 |
| | FcR9_N | Val192Asn | 0 |
| | FcR9_D | Val192Asp | 0 |
| | FcR9_C | Val192Cys | 0 |
| | FcR9_Q | Val192Gln | 0 |
| | FcR9_E | Val192Glu | 0 |
| | FcR9_G | Val192Gly | 0 |
| | FcR9_H | Val192His | 0 |
| | FcR9_K | Val192Lys | 0 |
| | FcR9_M | Val192Met | 0 |
| | FcR9_P | Val192Pro | 0 |
| | FcR9_S | Val192Ser | 0 |
| | FcR9_T | Val192Thr | 0 |
| | FcR9_W | Val192Trp | 0 |

Reference Example 3

This was carried out in the same manner as Reference Example 2, except for using transformants expressing the Fc-binding protein FcR9 (SEQ ID NO: 20) disclosed in Japanese Unexamined Patent Publication No. 2016-169197 (PTL 3) as the transformants.

The results are shown in Table 14. The expression level of the Fc-binding protein per 1 L of culture solution was 1.4 mg. These results show that transformants expressing Fc-binding protein having the amino acid substitution Val192Ile, Val192Ile or Val192Tyr introduced into FcR9 have vastly increased expression levels compared to transformants expressing FcR9.

Reference Example 4

This was carried out in the same manner as Reference Example 2, except for using transformants expressing Fc-binding proteins having the amino acid residue at position 192 of FcR9 (SEQ ID NO: 20) (position 176 in SEQ ID NO: 1) replaced with phenylalanine (hereunder indicated as Val192Phe), arginine (hereunder indicated as Val192Arg), leucine (hereunder indicated as Val192Leu), asparagine (hereunder indicated a Val192Asn), aspartic acid (hereunder indicated as Val192Asp), cysteine (hereunder indicated as Val192Cys), glutamine (hereunder indicated as Val192Gln), glutamic acid (hereunder indicated as Val192Glu), glycine (hereunder indicated as Val192Gly), histidine (hereunder indicated as Val192His), lysine (hereunder indicated as Val192Lys), methionine (hereunder indicated as Val192Met), proline (hereunder indicated as Val192Pro), serine (hereunder indicated as Val192Ser), threonine (hereunder indicated as Val192Thr) or tryptophan (hereunder indicated as Val192Trp) as the transformants.

The results are shown in Table 14. The expression levels of the Fc-binding proteins per 1 L of culture solution were all zero or <1 mg.

Reference Example 5: Evaluation of Binding Affinity Between Fc-Binding Protein and IgG1

(1) Of the transformants obtained in Reference Example 1, the transformants expressing FcR9_I (SEQ ID NO: 24) or FcR_A (SEQ ID NO: 26) were each inoculated onto 100 mL of 2YT liquid medium containing 50 μg/mL kanamycin and precultured overnight at 37° C. by aerobic shake culture.

(2) This preculturing solution was inoculated at 10 mL into 1000 mL of 2YT liquid medium (16 g/L peptone, 10 g/L yeast extract and 5 g/L sodium chloride) containing 50 μg/mL added kanamycin, and aerobically shake cultured at 37° C.

(3) At 1.5 hours after the start of culturing, the culturing temperature was lowered to 20° C. and shake culturing was continued for 30 minutes. Next, IPTG was added to a final concentration of 0.01 mM, and aerobic shake culturing was continued overnight at 20° C.

(4) Upon completion of culturing, the cells were collected by centrifugal separation and suspended in buffer (20 mM Tris-HCl buffer containing 150 mM NaCl (pH 7.4)) and subjected to ultrasonic disruption. The supernatant was then collected by centrifugal separation.

(5) The collected supernatant was passed through a column packed with Ni Sepharose6 Fast Flow (GE Healthcare) and thoroughly washed with wash buffer (20 mM Tris-HCl buffer containing 150 mM NaCl (pH 7.4)), after which it was eluted with elution buffer (20 mM Tris-HCl buffer containing 150 mM NaCl and 500 mM imidazole (pH 7.4)) and the elution fraction was recovered.

(6) The elution fraction recovered in (5) was passed through a column packed with IgG Sepharose6 Fast Flow (GE Healthcare) and thoroughly washed with wash buffer (20 mM Tris-HCl buffer containing 150 mM NaCl (pH 7.4)), after which it was eluted with elution buffer (100 mM glycine buffer containing (pH 3.0)) and the elution fraction was recovered.

(7) The affinity between IgG1 and each Fc-binding protein recovered as the elution fraction in (6) was evaluated by the surface plasmon resonance method. For measurement of the affinity using the surface plasmon resonance method, a Biacore T100 (GE Healthcare) was used as the measuring apparatus, a Sensor Chip CM5 (GE Healthcare) was used as the sensor chip and Biacore T100 Evaluation Software (GE Healthcare) was used as the analysis software.

(8) An Amine Coupling Kit (GE Healthcare) was used for flow of a solution comprising IgG1 (product of Sigma-Aldrich) diluted with HBS-EP (GE Healthcare) on a sensor chip immobilizing the Fc-binding protein, to obtain a sensorgram. Curve fitting was carried out based on the sensorgram to calculate the affinity for IgG1.

The results of calculating the affinity for IgG1 are shown in Table 15. In Table 15, a lower $K_D$ value (dissociation constant) indicates higher affinity (binding affinity). The $K_D$ values of FcR9_I (SEQ ID NO: 24) and FcR9_A (SEQ ID NO: 26) were $6.0 \times 10^{-8}$ M and $3.6 \times 10^{-8}$ M, respectively.

Reference Example 6

This was carried out in the same manner as Reference Example 5, except for using transformants expressing the Fc-binding protein FcR9 (SEQ ID NO: 20) disclosed in Japanese Unexamined Patent Publication No. 2016-169197 (PTL 3) as the transformants.

The results of calculating the affinity for IgG1 are shown in Table 15. The $K_D$ value of FcR9 was $7.7 \times 10^{-8}$ M, which was affinity equivalent to FcR9_I (SEQ ID NO: 24) and FcR9_A (SEQ ID NO: 26). This suggests that FcR9_I and FcR9_A, as forms of the Fc-binding protein of the invention, similar to FcR9, can be used as antibody adsorbents for process analysis and separation in the production of an antibody drug, by immobilization on an insoluble support.

TABLE 15

| Fc-binding protein | | Binding rate constant ka [1/Ms] | Binding rate constant kd [1/s] | Dissociation constant $K_D$ [M] |
|---|---|---|---|---|
| Reference Example | Name | Amino acid substitution | | |
| Reference Example 5 | FcR9_I | Val192Ile | $2.0 \times 10^5$ | $1.2 \times 10^{-2}$ | $6.0 \times 10^{-8}$ |
| | FcR9_A | Val192Ala | $1.0 \times 10^5$ | $3.5 \times 10^{-3}$ | $3.6 \times 10^{-8}$ |
| Reference Example 6 | FcR9 | — | $4.1 \times 10^5$ | $3.1 \times 10^{-2}$ | $7.7 \times 10^{-8}$ |
| Reference Example 7 | FcR9_F | Val192Phe | $0.9 \times 10^5$ | $3.0 \times 10^{-1}$ | $3.3 \times 10^{-6}$ |

Reference Example 7

This was carried out in the same manner as Reference Example 5, except for using transformants expressing Fc-binding protein (FcR_F), having phenylalanine substituting for valine at position 192 of FcR9 (SEQ ID NO: 20) (position 176 in SEQ ID NO: 1), as the transformants.

The results of calculating the affinity for IgG1 are shown in Table 15. The $K_D$ value of FcR9_F was $3.3 \times 10^{-6}$ M, thus confirming that it has lower affinity than the Fc-binding proteins of the invention, FcR9_I (SEQ ID NO: 24) and FcR_A (SEQ ID NO: 26), as well as FcR9 (SEQ ID NO: 20).

The invention claimed is:

1. An Fc-binding protein comprising at least the amino acid residues from glycine at position 33 to glutamine at position 208 of the amino acid sequence listed as SEQ ID NO: 7, 9 or 11.

2. A polynucleotide encoding an Fc-binding protein comprising at least the amino acid residues from glycine at position 33 to glutamine at position 208 of the amino acid sequence listed as SEQ ID NO: 7, 9 or 11.

3. An expression vector comprising the polynucleotide according to claim 2.

4. A transformant capable of producing Fc-binding protein, obtained by transforming a host with the expression vector according to claim 3.

5. The transformant according to claim 4, wherein the host is *E. coli*.

6. A method for producing Fc-binding protein, comprising producing Fc-binding protein by culturing the transformant according to claim 4, and recovering the produced Fc-binding protein from the cultured product.

7. Antibody adsorbent obtained by immobilizing the Fc-binding protein according to claim 1 on an insoluble support.

8. An antibody separating method comprising adding an antibody-containing solution to a column packed with the adsorbent according to claim 7, and adsorbing the antibody onto the adsorbent, and using an eluent to elute the antibody adsorbed on the adsorbent.

9. The separating method according to claim 8, wherein antibodies with different sugar chain structures are separated based on differences in their affinity for Fc-binding protein.

* * * * *

SEQUENCE LISTING

```
<160> NUMBER OF SEQ ID NOS: 29

<210> SEQ ID NO 1
<211> LENGTH: 254
<212> TYPE: PRT
<213> ORGANISM: Homo sapiens
<300> PUBLICATION INFORMATION:
<308> DATABASE ACCESSION NUMBER: UniProt P08637
<309> DATABASE ENTRY DATE: 1990-08-01
<313> RELEVANT RESIDUES IN SEQ ID NO: (1)..(254)

<400> SEQUENCE: 1

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125
```

```
His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taatacgact cactataggg                                              20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tatgctagtt attgctcag                                               19

<210> SEQ ID NO 4
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MalE-CD16a-6His

<400> SEQUENCE: 4
```

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Val Phe Leu Glu Pro
        35                  40                  45

Gln Trp Tyr Arg Val Leu Glu Lys Asp Ser Val Thr Leu Lys Cys Gln
    50                  55                  60

Gly Ala Tyr Ser Pro Glu Asp Asn Ser Thr Gln Trp Phe His Asn Glu
65                  70                  75                  80
```

```
Ser Leu Ile Ser Ser Gln Ala Ser Ser Tyr Phe Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
            115                 120                 125

Ala Pro Arg Trp Val Phe Lys Glu Glu Asp Pro Ile His Leu Arg Cys
        130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
            195                 200                 205

Gly Gly His His His His His His
            210                 215

<210> SEQ ID NO 5
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR35c

<400> SEQUENCE: 5

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Gln Asp Ser Val Thr Leu Lys Cys Arg
    50                  55                  60

Gly Ala His Ser Pro Asp Asp Asp Ser Thr Gln Trp Phe His Asn Glu
65                  70                  75                  80

Ser Leu Ile Pro Ser Gln Ala Ser Ser Phe Ile Ile Asp Ser Ala Ser
                85                  90                  95

Val Glu Asp Ser Gly Glu Tyr Arg Cys Gln Thr Ser Leu Ser Thr Leu
            100                 105                 110

Ser Glu Pro Val Leu Leu Glu Val His Ile Gly Trp Leu Leu Leu Gln
            115                 120                 125

Ala Pro Arg Trp Glu Phe Val Glu Gly Glu Pro Ile His Leu Arg Cys
        130                 135                 140

His Ser Trp Arg Asn Thr Ala Leu His Lys Val Met Phe Leu Gln Asn
145                 150                 155                 160

Gly Lys Val Arg Lys Tyr Phe His His Asn Ser Asp Phe Val Ile Pro
                165                 170                 175

Lys Ala Thr Leu Glu Asp Ser Gly Ser Tyr Ser Cys Arg Gly Leu Val
            180                 185                 190

Gly Arg Lys Asn Val Ser Ser Glu Ala Val Glu Ile Thr Val Thr Pro
            195                 200                 205
```

Gly Gly His His His His His His
    210                 215

<210> SEQ ID NO 6
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR35c

<400> SEQUENCE: 6
atgaaaataa aaacaggtgc acgcatcctc gcattatccg cattaacgac gatgatgttt      60
tccgcctcgg ctctcgccaa aatcgaagaa gccatgggca tgcgtaccgg agatatgccg     120
aaagcggagg tgattctgga accgccgtgg aatcgcgtgc tggagcaaga ttcagtgacc     180
cttaaatgcc ggggcgcgca tagcccggat gatgacagca cccagtggtt ccacaatgaa     240
agcctgattc ccagccaggc gagcagcttc attattgatt cggcgtcggt ggaagatagc     300
ggcgaatatc gttgccagac cagcctgagc accctgagcg aaccggtgct gctggaggtg     360
cacatcgggt ggcttctgtt acaggctcca cggtgggagt tcgtagaggg ggaaccgatt     420
catctgcggt gtcactcctg gaggaatacc gccctgcata agtgatgtt cctgcaaaac      480 ggcaaggtcc gcaagtattt ccaccacaac tccgacttcg ttattcccaa agcgacgctg     540
gaggacagcg gcagctattc ctgccgtggg ctggtgggca gaaaaatgt gagcagcgag      600 gccgtggaaa ttaccgttac cccagggggc catcatcatc atcatcat                  648

<210> SEQ ID NO 7
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR35d

<400> SEQUENCE: 7

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Gln Asp Ser Val Thr Leu Lys Cys Arg
    50                  55                  60

Gly Ala His Ser Pro Asp Asp Ser Thr Gln Trp Phe His Asn Glu
65                  70                  75                  80

Arg Leu Ile Pro Ser Gln Ala Ser Ser Phe Ile Ile Asp Ser Ala Ser
            85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Val Glu Gly Glu Pro Ile His Leu Arg Cys
    130                 135                 140

```
His Ser Trp Arg Asn Thr Ala Leu His Lys Val Met Phe Leu Gln Asn
145                 150                 155                 160

Gly Lys Val Arg Lys Tyr Phe His His Asn Ser Asp Phe Val Ile Pro
            165                 170                 175

Lys Ala Thr Leu Glu Asp Ser Gly Ser Tyr Ser Cys Arg Gly Leu Val
            180                 185                 190

Gly Arg Lys Lys Val Ser Ser Gly Ala Val Asp Ile Thr Val Thr Gln
        195                 200                 205

Gly Gly His His His His His His
        210                 215

<210> SEQ ID NO 8
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR35d

<400> SEQUENCE: 8
atgaaaataa aaacaggtgc acgcatcctc gcattatccg cattaacgac gatgatgttt    60
tccgcctcgg ctctcgccaa atcgaagaa gccatgggca tgcgtaccgg agatatgccg    120
aaagcggagg tgattctgga accgccgtgg aatcgcgtgc tggagcaaga ttcagtgacc    180
cttaaatgcc ggggcgcgca tagcccggat gatgacagca cccagtggtt ccacaatgaa    240
cgcctgattc ccagccaggc gagcagcttc attattgatt cggcgtcggt ggatgatagc    300
ggcgaatatc gttgccagac cagcctgagc accctgagcg atccggtgca gctggaggtg    360
cacatcgggt ggcttctgtt acaggctcca cggtgggagt tcgtagaggg ggaaccgatt    420
catctgcggt gtcactcctg gaggaatacc gccctgcata agtgatgtt cctgcaaaac    480 ggcaaggtcc gcaagtattt ccaccacaac tccgacttcg ttattcccaa agcgacgctg    540
gaggacagcg gcagctattc ctgccgtggg ctggtgggca gaaaaaaggt gagcagcggg    600
gccgtggaca ttaccgttac ccaaggggc catcatcatc atcatcat              648

<210> SEQ ID NO 9
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR36i

<400> SEQUENCE: 9

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Gln Asp Ser Val Thr Leu Lys Cys Arg
    50                  55                  60

Gly Ala His Ser Pro Asp Asp Asp Ser Thr Gln Trp Phe His Asn Glu
65                  70                  75                  80
```

Arg Leu Ile Pro Ser Gln Ala Ser Ser Phe Ile Ile Asp Ser Ala Ser
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Val Glu Gly Glu Pro Ile His Leu Arg Cys
    130                 135                 140

His Ser Trp Arg Asn Thr Ala Leu His Lys Val Met Phe Leu Gln Asn
145                 150                 155                 160

Gly Lys Val Arg Lys Tyr Phe His His Asn Ser Asp Phe Val Ile Pro
                165                 170                 175

Lys Ala Thr Leu Glu Asp Ser Gly Ser Tyr Ser Cys Arg Gly Leu Ile
            180                 185                 190

Gly Arg Lys Lys Val Ser Ser Gly Ala Val Asp Ile Thr Val Thr Gln
        195                 200                 205

Gly Gly His His His His His His
    210                 215

<210> SEQ ID NO 10
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR36i

<400> SEQUENCE: 10
atgaaaataa aaacaggtgc acgcatcctc gcattatccg cattaacgac gatgatgttt      60
tccgcctcgg ctctcgccaa atcgaagaa gccatgggca tgcgtaccgg agatatgccg      120
aaagcggagg tgattctgga accgccgtgg aatcgcgtgc tggagcaaga ttcagtgacc      180
cttaaatgcc ggggcgcgca tagcccggat gatgacagca cccagtggtt ccacaatgaa      240
cgcctgattc ccagccaggc gagcagcttc attattgatt cggcgtcggt ggatgatagc      300
ggcgaatatc gttgccagac cagcctgagc accctgagcg atccggtgca gctggaggtg      360
cacatcgggt ggcttctgtt acaggctcca cggtgggagt tcgtagaggg ggaaccgatt      420
catctgcggt gtcactcctg gaggaatacc gccctgcata agtgatgtt cctgcaaaac      480 ggcaaggtcc gcaagtattt ccaccacaac tccgacttcg ttattcccaa agcgacgctg      540
gaggacagcg gcagctattc ctgccgtggg ctgattggca gaaaaaggt gagcagcggg      600 gccgtggaca ttaccgttac ccaagggggc catcatcatc atcatcat              648

<210> SEQ ID NO 11
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR36a

<400> SEQUENCE: 11

Met Lys Ile Lys Thr Gly Ala Arg Ile Leu Ala Leu Ser Ala Leu Thr
1               5                   10                  15

```
Thr Met Met Phe Ser Ala Ser Ala Leu Ala Lys Ile Glu Glu Ala Met
            20                  25                  30

Gly Met Arg Thr Gly Asp Met Pro Lys Ala Glu Val Ile Leu Glu Pro
        35                  40                  45

Pro Trp Asn Arg Val Leu Glu Gln Asp Ser Val Thr Leu Lys Cys Arg
 50                  55                  60

Gly Ala His Ser Pro Asp Asp Ser Thr Gln Trp Phe His Asn Glu
 65              70                  75                  80

Arg Leu Ile Pro Ser Gln Ala Ser Ser Phe Ile Ile Asp Ser Ala Ser
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Val Glu Gly Glu Pro Ile His Leu Arg Cys
130                 135                 140

His Ser Trp Arg Asn Thr Ala Leu His Lys Val Met Phe Leu Gln Asn
145                 150                 155                 160

Gly Lys Val Arg Lys Tyr Phe His His Asn Ser Asp Phe Val Ile Pro
                165                 170                 175

Lys Ala Thr Leu Glu Asp Ser Gly Ser Tyr Ser Cys Arg Gly Leu Ala
            180                 185                 190

Gly Arg Lys Lys Val Ser Ser Gly Ala Val Asp Ile Thr Val Thr Gln
        195                 200                 205

Gly Gly His His His His His His
    210                 215

<210> SEQ ID NO 12
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR36a

<400> SEQUENCE: 12
atgaaaataa aaacaggtgc acgcatcctc gcattatccg cattaacgac gatgatgttt      60
tccgcctcgg ctctcgccaa aatcgaagaa gccatgggca tgcgtaccgg agatatgccg     120
aaagcggagg tgattctgga accgccgtgg aatcgcgtgc tggagcaaga ttcagtgacc     180
cttaaatgcc ggggcgcgca tagcccggat gatgacagca cccagtggtt ccacaatgaa     240
cgcctgattc ccagccaggc gagcagcttc attattgatt cggcgtcggt ggatgatagc     300
ggcgaatatc gttgccagac cagcctgagc accctgagcg atccggtgca gctggaggtg     360
cacatcgggt ggcttctgtt acaggctcca cggtgggagt tcgtagaggg ggaaccgatt     420
catctgcggt gtcactcctg gaggaatacc gccctgcata agtgatgtt cctgcaaaac     480 ggcaaggtcc gcaagtattt ccaccacaac tccgacttcg ttattcccaa agcgacgctg     540
gaggacagcg gcagctattc ctgccgtggg ctggcgggca gaaaaaaggt gagcagcggg     600
gccgtggaca ttaccgttac ccaaggggggc atcatcatc atcatcat                  648

<210> SEQ ID NO 13
<211> LENGTH: 53
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 13
catatgaaaa taaaaacagg tgcacgcatc ctcgcattat ccgcattaac gac            53

<210> SEQ ID NO 14
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cccaagctta tccgcaggta tcgttgcggc acccttgggt aacggtaatg tccacggccc    60
cgctg                                                                65

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgtggtatgg ctgtgcagg                                                 19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcggcatggg gtcaggtg                                                  18

<210> SEQ ID NO 17
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR36i_Cys

<400> SEQUENCE: 17

Met Lys Tyr Leu Leu Ser Thr Ala Ala Ala Gly Leu Leu Leu Leu Ala
1               5                   10                  15

Ala Gln Pro Ala Met Ala Met Gly Met Arg Thr Gly Asp Met Pro Lys
            20                  25                  30

Ala Glu Val Ile Leu Glu Pro Pro Trp Asn Arg Val Leu Glu Gln Asp
        35                  40                  45

Ser Val Thr Leu Lys Cys Arg Gly Ala His Ser Pro Asp Asp Asp Ser
    50                  55                  60

Thr Gln Trp Phe His Asn Glu Arg Leu Ile Pro Ser Gln Ala Ser Ser
65                  70                  75                  80

```
Phe Ile Ile Asp Ser Ala Ser Val Asp Asp Ser Gly Glu Tyr Arg Cys
             85                  90                  95

Gln Thr Ser Leu Ser Thr Leu Ser Asp Pro Val Gln Leu Glu Val His
            100                 105                 110

Ile Gly Trp Leu Leu Leu Gln Ala Pro Arg Trp Glu Phe Val Glu Gly
            115                 120                 125

Glu Pro Ile His Leu Arg Cys His Ser Trp Arg Asn Thr Ala Leu His
        130                 135                 140

Lys Val Met Phe Leu Gln Asn Gly Lys Val Arg Lys Tyr Phe His His
145                 150                 155                 160

Asn Ser Asp Phe Val Ile Pro Lys Ala Thr Leu Glu Asp Ser Gly Ser
                165                 170                 175

Tyr Ser Cys Arg Gly Leu Ile Gly Arg Lys Lys Val Ser Ser Gly Ala
            180                 185                 190

Val Asp Ile Thr Val Thr Gln Gly Cys Arg Asn Asp Thr Cys Gly
            195                 200                 205
```

<210> SEQ ID NO 18
<211> LENGTH: 621
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR36i_Cys

<400> SEQUENCE: 18

```
atgaaatacc tgctgtcgac cgctgctgct ggtctgctgc tcctcgctgc ccagccggcg      60
atggccatgg gcatgcgtac cggagatatg ccgaaagcgg aggtgattct ggaaccgccg     120
tggaatcgcg tgctggagca agattcagtg acccttaaat gccggggcgc gcatagcccg     180
gatgatgaca gcacccagtg gttccacaat gaacgcctga ttcccagcca ggcgagcagc     240
ttcattattg attcggcgtc ggtggatgat agcggcgaat atcgttgcca gaccagcctg     300
agcaccctga gcgatccggt gcagctggag gtgcacatcg gtggcttctt gttacaggct     360
ccacggtggg agttcgtaga gggggaaccg attcatctgc ggtgtcactc ctggaggaat     420
accgccctgc ataaagtgat gttcctgcaa aacggcaagg tccgcaagta tttccaccac     480
aactccgact cgttattcc caaagcgacg ctggaggaca gcggcagcta tcctgccgt      540 gggctgattg gcagaaaaaa ggtgagcagc ggggccgtgg acattaccgt tacccaaggg     600
tgccgcaacg atacctgcgg a                                               621
```

<210> SEQ ID NO 19
<211> LENGTH: 254
<212> TYPE: PRT
<213> ORGANISM: Homo sapiens
<300> PUBLICATION INFORMATION:
<308> DATABASE ACCESSION NUMBER: GenBank AAH17865.1

<400> SEQUENCE: 19

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45
```

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 20
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR9

<400> SEQUENCE: 20

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Ile Leu Glu Pro
            35                  40                  45

Gln Trp Asn Arg Val Leu Glu Lys Asp Ser Val Thr Leu Lys Cys Arg
50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
                100                 105                 110

Ser Asp Pro Val Gln Leu Glu Val His Ile Gly Trp Leu Leu Leu Gln
            115                 120                 125

Ala Pro Arg Trp Glu Phe Lys Glu Gly Asp Pro Ile His Leu Arg Cys
130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
            165                 170                 175

Lys Ala Thr Leu Lys Asp Ser Gly Ser Tyr Ser Cys Arg Gly Leu Val
        180                 185                 190

Gly Ser Lys Asn Val Ser Ser Glu Thr Val Asn Ile Thr Ile Thr Gln
    195                 200                 205

Gly Gly His His His His His His
    210                 215

<210> SEQ ID NO 21
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR9

<400> SEQUENCE: 21
atgaaaataa aaacaggtgc acgcatcctc gcattatccg cattaacgac gatgatgttt      60
tccgcctcgg ctctcgccaa atcgaagaa gccatgggca tgcgtaccga agatctgccg     120
aaagcggagg tgattctgga accgcagtgg aatcgcgtgc tggagaaaga ttctgtgacc     180
cttaaatgcc ggggcgcgta tagccccgaa gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata aagtgaccta cctgcaaaac     480
ggcaagggcc gcaagtattt ccaccacaac tccgacttct atattcccaa agcgacgctg     540
aaggacagcg gcagctattc ctgccgtggg ctggtgggca gcaaaaatgt gagcagcgag     600
accgtgaata ttaccattac ccaaggggc catcatcatc atcatcat                   648

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(16)
<223> OTHER INFORMATION: a, c, g, or t

<400> SEQUENCE: 22
catttttgct gccmnncagc ccacggcagg                                       30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(16)
<223> OTHER INFORMATION: a, c, g, or t -continued

<400> SEQUENCE: 23
cctgccgtgg gctgnnkggc agcaaaaatg                                              30

<210> SEQ ID NO 24
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR9_I

<400> SEQUENCE: 24

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Ile Leu Glu Pro
            35                  40                  45

Gln Trp Asn Arg Val Leu Glu Lys Asp Ser Val Thr Leu Lys Cys Arg
        50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Ile
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 25
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR9_I

<400> SEQUENCE: 25
atgaaaataa aaacaggtgc acgcatcctc gcattatccg cattaacgac gatgatgttt         60
tccgcctcgg ctctcgccaa aatcgaagaa gccatgggca tgcgtaccga agatctgccg        120
aaagcggagg tgattctgga accgcagtgg aatcgcgtgc tggagaaaga ttctgtgacc        180

```
cttaaatgcc ggggcgcgta tagcccggaa gataacagca cccagtggtt ccacaatgaa    240
agcctgattt ccagccaggc gagcagctac cttattgatg cggcgacggt ggatgatagc    300
ggcgaatatc gttgccagac cagcctgagc accctgagcg atccggtgca gctggaggtg    360
cacatcgggt ggcttctgtt acaggctcca cggtgggagt tcaaagaggg ggatccgatt    420
catctgcggt gtcactcctg gaagaatacc gccctgcata agtgaccta cctgcaaaac    480 ggcaagggcc gcaagtattt ccaccacaac tccgacttct atattcccaa agcgacgctg    540
aaggacagcg gcagctattc ctgccgtggg ctgattggca gcaaaaatgt gagcagcgag    600
accgtgaata ttaccattac ccaaggggc catcatcatc atcatcat    648
```

```
<210> SEQ ID NO 26
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FcR9_A

<400> SEQUENCE: 26
```

| | | | | | | | | | | | | | | | |
|---|---|---|---|---|---|---|---|---|---|---|---|---|---|---|---|
| Met | Lys | Ile | Lys | Thr | Gly | Ala | Arg | Ile | Leu | Ala | Leu | Ser | Ala | Leu | Thr |
| 1 | | | | 5 | | | | | 10 | | | | | 15 | |
| Thr | Met | Met | Phe | Ser | Ala | Ser | Ala | Leu | Ala | Lys | Ile | Glu | Glu | Ala | Met |
| | | | | 20 | | | | | 25 | | | | | 30 | |
| Gly | Met | Arg | Thr | Glu | Asp | Leu | Pro | Lys | Ala | Glu | Val | Ile | Leu | Glu | Pro |
| | | | 35 | | | | | 40 | | | | | 45 | | |
| Gln | Trp | Asn | Arg | Val | Leu | Glu | Lys | Asp | Ser | Val | Thr | Leu | Lys | Cys | Arg |
| | 50 | | | | | 55 | | | | | 60 | | | | |
| Gly | Ala | Tyr | Ser | Pro | Glu | Asp | Asn | Ser | Thr | Gln | Trp | Phe | His | Asn | Glu |
| 65 | | | | | 70 | | | | | 75 | | | | | 80 |
| Ser | Leu | Ile | Ser | Ser | Gln | Ala | Ser | Ser | Tyr | Leu | Ile | Asp | Ala | Ala | Thr |
| | | | | 85 | | | | | 90 | | | | | 95 | |
| Val | Asp | Asp | Ser | Gly | Glu | Tyr | Arg | Cys | Gln | Thr | Ser | Leu | Ser | Thr | Leu |
| | | | | 100 | | | | | 105 | | | | | 110 | |
| Ser | Asp | Pro | Val | Gln | Leu | Glu | Val | His | Ile | Gly | Trp | Leu | Leu | Leu | Gln |
| | | | 115 | | | | | 120 | | | | | 125 | | |
| Ala | Pro | Arg | Trp | Glu | Phe | Lys | Glu | Gly | Asp | Pro | Ile | His | Leu | Arg | Cys |
| | 130 | | | | | 135 | | | | | 140 | | | | |
| His | Ser | Trp | Lys | Asn | Thr | Ala | Leu | His | Lys | Val | Thr | Tyr | Leu | Gln | Asn |
| 145 | | | | | 150 | | | | | 155 | | | | | 160 |
| Gly | Lys | Gly | Arg | Lys | Tyr | Phe | His | His | Asn | Ser | Asp | Phe | Tyr | Ile | Pro |
| | | | | 165 | | | | | 170 | | | | | 175 | |
| Lys | Ala | Thr | Leu | Lys | Asp | Ser | Gly | Ser | Tyr | Ser | Cys | Arg | Gly | Leu | Ala |
| | | | 180 | | | | | 185 | | | | | 190 | | |
| Gly | Ser | Lys | Asn | Val | Ser | Ser | Glu | Thr | Val | Asn | Ile | Thr | Ile | Thr | Gln |
| | | | 195 | | | | | 200 | | | | | 205 | | |
| Gly | Gly | His | His | His | His | His | His | | | | | | | | |
| | | | 210 | | | | | 215 | | | | | | | |

```
<210> SEQ ID NO 27
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<223> OTHER INFORMATION: Polynucleotide encoding FcR9_A

<400> SEQUENCE: 27

```
atgaaaataa aaacaggtgc acgcatcctc gcattatccg cattaacgac gatgatgttt    60
tccgcctcgg ctctcgccaa aatcgaagaa gccatgggca tgcgtaccga agatctgccg   120
aaagcggagg tgattctgga accgcagtgg aatcgcgtgc tggagaaaga ttctgtgacc   180
cttaaatgcc ggggcgcgta tagcccggaa gataacagca cccagtggtt ccacaatgaa   240
agcctgattt ccagccaggc gagcagctac cttattgatg cggcgacggt ggatgatagc   300
ggcgaatatc gttgccagac cagcctgagc accctgagcg atccggtgca gctggaggtg   360
cacatcgggt ggcttctgtt acaggctcca cggtgggagt tcaaagaggg ggatccgatt   420
catctgcggt gtcactcctg gaagaatacc gccctgcata agtgaccta cctgcaaaac   480
ggcaagggcc gcaagtattt ccaccacaac tccgacttct atattcccaa agcgacgctg   540
aaggacagcg gcagctattc ctgccgtggg ctggcgggca gcaaaaatgt gagcagcgag   600
accgtgaata ttaccattac ccaagggggc catcatcatc atcatcat              648
```

<210> SEQ ID NO 28
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: FcR9_Y

<400> SEQUENCE: 28

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Ile Leu Glu Pro
        35                  40                  45

Gln Trp Asn Arg Val Leu Glu Lys Asp Ser Val Thr Leu Lys Cys Arg
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Tyr
            180                 185                 190

Gly Ser Lys Asn Val Ser Ser Glu Thr Val Asn Ile Thr Ile Thr Gln
        195                 200                 205
```

```
Gly Gly His His His His His His
    210                 215

<210> SEQ ID NO 29
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Polynucleotide encoding FcR9_Y

<400> SEQUENCE: 29
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgattctgga accgcagtgg aatcgcgtgc tggagaaaga ttctgtgacc     180
cttaaatgcc ggggcgcgta tagcccggaa gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata aagtgaccta cctgcaaaac     480
ggcaagggcc gcaagtattt ccaccacaac tccgacttct atattcccaa agcgacgctg     540
aaggacagcg gcagctattc ctgccgtggg ctgtatggca gcaaaaatgt gagcagcgag     600
accgtgaata ttaccattac ccaaggggc catcatcatc atcatcat              648
```